United States Patent
Zhang et al.

(10) Patent No.: US 8,685,743 B2
(45) Date of Patent: Apr. 1, 2014

(54) REAL-TIME, SINGLE-STEP BIOASSAY USING NANOPLASMONIC RESONATOR WITH ULTRA-HIGH SENSITIVITY

(75) Inventors: Xiang Zhang, Alamo, CA (US); Jonathan A. Ellman, Guilford, CT (US); Fanqing Frank Chen, Moraga, CA (US); Kai-Hang Su, Seoul (KR); Qi-Huo Wei, Kent, OH (US); Cheng Sun, Evanston, IL (US)

(73) Assignee: The Regents of the University of California, Oakland, CA (US)

( * ) Notice: Subject to any disclaimer, the term of this patent is extended or adjusted under 35 U.S.C. 154(b) by 837 days.

(21) Appl. No.: 12/772,118

(22) Filed: Apr. 30, 2010

(65) Prior Publication Data

US 2011/0058164 A1 Mar. 10, 2011

Related U.S. Application Data

(63) Continuation of application No. PCT/US2008/082266, filed on Nov. 3, 2008.

(60) Provisional application No. 60/984,859, filed on Nov. 2, 2007.

(51) Int. Cl.
*G01N 21/00* (2006.01)

(52) U.S. Cl.
USPC ........ 436/164; 436/166; 436/169; 422/82.05; 422/82.06; 422/82.07; 422/82.08

(58) Field of Classification Search
None
See application file for complete search history.

(56) References Cited

U.S. PATENT DOCUMENTS

| | | | |
|---|---|---|---|
| 5,306,403 A | 4/1994 | Vo-Dinh | |
| 6,002,471 A | 12/1999 | Quake | |
| 6,174,677 B1 | 1/2001 | Vo-Dinh | |
| 7,122,384 B2 | 10/2006 | Prober et al. | |
| 2006/0215154 A1 | 9/2006 | Chan et al. | |
| 2006/0273245 A1* | 12/2006 | Kim et al. | 250/226 |

FOREIGN PATENT DOCUMENTS

| WO | 2008/018933 A2 | 2/2008 |
|---|---|---|
| WO | WO 2009/094058 | 7/2009 |

OTHER PUBLICATIONS

Su et al. "Tunable and augmented plasmon resonances of Au/SiO2/Au nanodisks", Appl. Phys. Lett., 2006, v. 88, pp. 063118-1-063118-3.*
PCT International Search Report and Written Opinion dated Aug. 31, 2009 issued in PCT/US2008/82266 (WO 2009/094058).
PCT International Preliminary Report on Patentability dated May 4, 2010 issued in PCT/US2008/82266 (WO 2009/094058).
Chinese Office Action dated Oct. 10, 2011 issued in 200880123805.8.

(Continued)

*Primary Examiner* — Yelena G Gakh
(74) *Attorney, Agent, or Firm* — Tom Hunter; Weaver Austin Villeneuve & Sampson LLP

(57) ABSTRACT

A nanoplasmonic resonator (NPR) comprising a metallic nanodisk with alternating shielding layer(s), having a tagged biomolecule conjugated or tethered to the surface of the nanoplasmonic resonator for highly sensitive measurement of enzymatic activity. NPRs enhance Raman signals in a highly reproducible manner, enabling fast detection of protease and enzyme activity, such as Prostate Specific Antigen (paPSA), in real-time, at picomolar sensitivity levels. Experiments on extracellular fluid (ECF) from paPSA-positive cells demonstrate specific detection in a complex bio-fluid background in real-time single-step detection in very small sample volumes.

17 Claims, 7 Drawing Sheets

(56) References Cited

OTHER PUBLICATIONS

Chinese Second Office Action dated Aug. 16, 2012 issued in 200880123805.8.
Chinese Third Office Action dated Apr. 15, 2013 issued in 200880123805.8.
Altschuh, D. et al. (1994). "Modulation of the Enzymatic Activity of Papain by Interdomain Residues Remote From the Active Site," Protein Engineering 7(6):769-775.
Canto, E. I. et al. (2004). "Molecular Diagnosis of Prostate Cancer," Current Urology Reports 5(3):203-211.
Cao, Y. C. (2003). "Raman Dye-Labeled Nanoparticle Probes for Proteins," Journal of the American Chemical Society 125(48):14676-14677.
Cao, Y. C. et al. (Aug. 30, 2002). "Nanoparticles With Raman Spectroscopic Fingerprints for DNA and RNA Detection," Science 297(5586):1536-1540.
Caplan, A. et al. (2002). "Prostate-Specific Antigen and the Early Diagnosis of Prostate Cancer," American Journal of Clinical Pathology 117(Suppl.1):S104-S108.
Clements, J. A. et al. (2004). "The Tissue Kallikrein Family of Serine Proteases: Functional Roles in Human Disease and Potential as Clinical Biomarkers," Critical Reviews in Clinical Laboratory Sciences 41(3):265-312.
Denmeade, S. R. et al. (2004). "The Role of Prostate-Specific Antigen in the Clinical Evaluation of Prostatic Disease," BJU International 93(Suppl. 1):10-15.
Denmeade, S. R. et al. (Mar. 2002). "A History of Prostate Cancer Treatment," Nature Reviews Cancer 2:389-396.
Denmeade, S. R. et al. (Nov. 1, 1997). "Specific and Efficient Peptide Substrates for Assaying the Proteolytic Activity of Prostate-Specific Antigen," Cancer Research 57:4924-4930.
Denmeades, S. R. et al. (Jul. 2, 2003). "Prostate-Specific Antigen-Activated Thapsigargin Prodrug As Targeted Therapy for Prostate Cancer," Journal of the National Cancer Institute 95(13):990-1000.
Freeman, R. G. et al. (Mar. 17, 1995). "Self-Assembled Metal Colloid Monolayers: An Approach to SERS Substrates," Science 267:1629-1632.
Gretzer, M. B. et al. (2003). "PSA Markers in Prostate Cancer Detection," Urologic Clinics of North America 30:677-686.
Gronberg, H. (Mar. 8, 2003). "Prostate Cancer Epidemiology," The Lancet 361:859-863.
Grow, A. E. et al. (2003). "New Biochip Technology for Label-Free Detection of Pathogens and Their Toxins," Journal of Microbiological Methods 53:221-233.
Haese, A. et al. (2004). "Prostate-Specific Antigen and Related Isoforms in the Diagnosis and Management of Prostate Cancer," Current Urology Reports 5(3):231-240.
Haynes, C. L. et al. "Plasmon-Sampled Surface-Enhanced Raman Excitation Spectroscopy," Journal of Physical Chemistry B 107(30):7426-7433.
Jackson, J. B. et al. (Dec. 28, 2004). "Surface-Enhanced Raman Scattering on Tunable Plasmonic Nanoparticle Substrates," Proceedings of the National Academy of Sciences of the United States of America 101 (52):17930-17935.
Kahl, M. et al. (1998). "Periodically Structured Metallic Substrates for SERS," Sensors and Actuators B: Chemical 51:285-291.
Klimpel, K. R. et al. (1994). "Anthrax Toxin Lethal Factor Contains a Zinc Metalloprotease Consensus Sequence Which is Required for Lethal Toxin Activity," Molecular Microbiology 13(6):1093-1110.
Kneipp, K. et al. (Oct. 10, 1999). "Surface-Enhanced Raman Scattering: A New Tool for Biomedical Spectroscopy," Current Science (Bangalore) 77(7):915-924.
Lyandres, O. et al. (Oct. 1, 2005). "Real-Time Glucose Sensing by Surface-Enhanced Raman Spectroscopy in Bovine Plasma Facilitated by a Mixed Decanethiol/Mercaptohexanol Partition Layer," Analytical Chemistry 77 (19):6134-6139.
Moskovits, M. (Jul. 1985). "Surface-Enhanced Spectroscopy," Reviews of Modern Physics 57(3, Part 1):783-826.
Nie, S. et al. (Feb. 21, 1997). "Probing Single Molecules and Single Nanoparticles by Surface-Enhanced Raman Scattering," Science 275:1102-1106.
Nithipatikom, K. et al. (2003). "Characterization and Application of Raman Labels for Confocal Raman Microspectroscopic Detection of Cellular Proteins in Single Cells," Analytical Biochemistry 322:198-207.
Paetzel, M. et al. (Jan. 1997). "Catalytic Hydroxyl/Amine Dyads Within Serine Proteases," Trends in Biochemical Sciences 22:28-31.
Schecter, I. et al. (1967). "On the Size of the Active Site in Proteases. I. Papain," Biochemical and Biophysical Research Communications 27(2):157-162.
Spinelli, S. et al. (1991). "The Three-Dimensional Structure of the Aspartyl Protease From the HIV-1 Isolate BRU," Biochimie 73:1391-1396.
Stuart, D. A. (2006). "Surface-Enhanced Raman Spectroscopy of Half-Mustard Agent," The Analyst 131:568-572.
Su, K. et al. (2006). "Raman Enhancement Factor of a Single Tunable Nanoplasmonic Resonator," Journal of Physical Chemistry B 110(9):3964-3968.
Sylvia, J. M. et al. (Dec. 1, 2000). "Surface-Enhanced Raman Detection of 2,4-Dinitrotoluene Impurity Vapor As a Marker to Locate Landmines," Analytical Chemistry 72(23):5834-5840.
Vo-Dinh, T. et al. (2005). "Surface-Enhanced Raman Scattering for Medical Diagnostics and Biological Imaging," Journal of Raman Spectroscopy 36:640-647.
Wu, P. et al. (2004). "Immunopeptidometric Assay for Enzymatically Active Prostate-Specific Antigen," Clinical Chemistry 50(1):125-129.
Wu, P. et al. (2004). "Separation of Enzymatically Active and Inactive Prostate-Specific Antigen (PSA) by Peptide Affinity Chromatography," The Prostate 58:345-353.
Yonzon, C. R. et al. (Jan. 1, 2004). "A Glucose Biosensor Based on Surface-Enhanced Raman Scattering: Improved Partition Layer, Temporal Stability, Reversibility, and Resistance to Serum Protein Interference," Analytical Chemistry 76(1):78-85.

* cited by examiner

SEQUENCE LISTING

<160> NUMBER OF SEQ ID NOS: 17

<210> SEQ ID NO 1
<211> LENGTH: 11
<212> TYPE: PRT
<213> ORGANISM: Artificial
<220> FEATURE:
<223> OTHER INFORMATION: Synthetic PSA-specific peptide substrate

<400> SEQUENCE: 1

His Ser Ser Lys Leu Gln Leu Ala Ala Ala Cys
1               5                   10

<210> SEQ ID NO 2
<211> LENGTH: 7
<212> TYPE: PRT
<213> ORGANISM: Artificial
<220> FEATURE:
<223> OTHER INFORMATION: Synthetic peptide substrate of cAMP-dependent
      protein kinase

<400> SEQUENCE: 2

Leu Arg Arg Ala Ser Leu Gly
1               5

<210> SEQ ID NO 3
<211> LENGTH: 9
<212> TYPE: PRT
<213> ORGANISM: Artificial
<220> FEATURE:
<223> OTHER INFORMATION: Synthetic peptide substrate of cAMP dependent
      protein kinase (PKA)

<400> SEQUENCE: 3

Gly Arg Thr Gly Arg Arg Asn Ser Ile
1               5

<210> SEQ ID NO 4
<211> LENGTH: 11
<212> TYPE: PRT
<213> ORGANISM: Artificial
<220> FEATURE:
<223> OTHER INFORMATION: Synthetic peptide substrate of protein kinase C
      (PKC)

<400> SEQUENCE: 4

Gln Lys Arg Pro Ser Gln Arg Ser Lys Tyr Leu
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic peptide substrate of protein kinase
      Akt/PKB

<400> SEQUENCE: 5

Arg Pro Arg Ala Ala Thr Phe
1               5

<210> SEQ ID NO 6
<211> LENGTH: 12
<212> TYPE: PRT
<213> ORGANISM: Artificial
<220> FEATURE:
<223> OTHER INFORMATION: Synthetic peptide substrate of Abl kinase

```
<400> SEQUENCE: 6

Glu Ala Ile Tyr Ala Ala Pro Phe Ala Lys Lys Lys
1               5                   10

<210> SEQ ID NO 7
<211> LENGTH: 15
<212> TYPE: PRT
<213> ORGANISM: Artificial
<220> FEATURE:
<223> OTHER INFORMATION: Synthetic peptide substrate of 5prime-AMP-
      activated protein kinase (AMPK)

<400> SEQUENCE: 7

His Met Arg Ser Ala Met Ser Gly Leu His Leu Val Lys Arg Arg
1               5                   10                  15

<210> SEQ ID NO 8
<211> LENGTH: 13
<212> TYPE: PRT
<213> ORGANISM: Artificial
<220> FEATURE:
<223> OTHER INFORMATION: Synthetic peptide substrate of Ca2+/calmodulin-
      dependent protein kinase

<400> SEQUENCE: 8

Lys Lys Ala Leu Arg Arg Gln Glu Thr Val Asp Ala Leu
1               5                   10

<210> SEQ ID NO 9
<211> LENGTH: 8
<212> TYPE: PRT
<213> ORGANISM: Artificial
<220> FEATURE:
<223> OTHER INFORMATION: Synthetic Peptide substrate of cyclin-
      dependent kinase 2 (cdc2)
<220> FEATURE:
<221> NAME/KEY: MOD_RES
<222> LOCATION: (1)..(1)
<223> OTHER INFORMATION: ACETYLATION

<400> SEQUENCE: 9

Ser Pro Gly Arg Arg Arg Arg Lys
1               5

<210> SEQ ID NO 10
<211> LENGTH: 7
<212> TYPE: PRT
<213> ORGANISM: Artificial
<220> FEATURE:
<223> OTHER INFORMATION: Synthetic peptide substrate of cyclin-dependent
      kinase 2 (Cdk2)

<400> SEQUENCE: 10

His His Ala Ser Pro Arg Lys
1               5

<210> SEQ ID NO 11
<211> LENGTH: 10
<212> TYPE: PRT
<213> ORGANISM: Artificial
<220> FEATURE:
<223> OTHER INFORMATION: Synthetic peptide substrate of cyclin-dependent
      kinase 5 (Cdk5)

<400> SEQUENCE: 11

Pro Lys Thr Pro Lys Lys Ala Lys Lys Leu
1               5                   10
```

```
<210> SEQ ID NO 12
<211> LENGTH: 18
<212> TYPE: PRT
<213> ORGANISM: Artificial
<220> FEATURE:
<223> OTHER INFORMATION: Synthetic peptide substrate of casein kinase 1
      (CK1)

<400> SEQUENCE: 12

Arg Arg Lys Asp Leu His Asp Asp Glu Glu Asp Glu Ala Met Ser Ile
1               5                   10                  15

Thr Ala

<210> SEQ ID NO 13
<211> LENGTH: 10
<212> TYPE: PRT
<213> ORGANISM: Artificial
<220> FEATURE:
<223> OTHER INFORMATION: Synthetic peptide substrate of CK2 alpha
      subunit or holoenzyme

<400> SEQUENCE: 13

Arg Arg Arg Asp Asp Asp Ser Asp Asp Asp
1               5                   10

<210> SEQ ID NO 14
<211> LENGTH: 14
<212> TYPE: PRT
<213> ORGANISM: Artificial
<220> FEATURE:
<223> OTHER INFORMATION: Synthetic peptide substrate of DYRK family
      protein kinases

<400> SEQUENCE: 14

Lys Lys Ile Ser Gly Arg Leu Ser Pro Ile Met Thr Glu Gln
1               5                   10

<210> SEQ ID NO 15
<211> LENGTH: 26
<212> TYPE: PRT
<213> ORGANISM: Artificial
<220> FEATURE:
<223> OTHER INFORMATION: Synthetic peptide substrate of GSK3 alpha and
      beta kinases
<220> FEATURE:
<221> NAME/KEY: MOD_RES
<222> LOCATION: (21)..(21)
<223> OTHER INFORMATION: PHOSPHORYLATION

<400> SEQUENCE: 15

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 16
<211> LENGTH: 15
<212> TYPE: PRT
<213> ORGANISM: Artificial
<220> FEATURE:
<223> OTHER INFORMATION: Synthetic peptide substrate of Src Kinase

<400> SEQUENCE: 16

Lys Val Glu Lys Ile Gly Glu Gly Thr Tyr Gly Val Val Tyr Lys
1               5                   10                  15

<210> SEQ ID NO 17
```

```
<211> LENGTH: 23
<212> TYPE: PRT
<213> ORGANISM: Artificial
<220> FEATURE:
<223> OTHER INFORMATION: Synthetic peptide substrate of checkpoint
      kinases CHK1 and CHK2

<400> SEQUENCE: 17

Lys Lys Lys Val Ser Arg Ser Gly Leu Tyr Arg Ser Pro Ser Met Pro
1               5                   10                  15

Glu Asn Leu Asn Arg Pro Arg
                20
```

REAL-TIME, SINGLE-STEP BIOASSAY USING NANOPLASMONIC RESONATOR WITH ULTRA-HIGH SENSITIVITY

CROSS-REFERENCE TO RELATED APPLICATIONS

This application claims priority to U.S. Provisional Patent Application No. 60/984,859, filed on Nov. 2, 2007, and International Patent Application No. PCT/US2008/082266, filed on Nov. 3, 2008, both of which are hereby incorporated by reference in their entirety.

STATEMENT OF GOVERNMENTAL SUPPORT

This work was supported by NSF Nano-scale Science and Engineering Center (DMI-0327077), NSFSST/Collaborative Research Program (DMI-0427679), and NASA Institute for Cell Mimetic Space Exploration (CMISE), under Award No. NCC2-1364; NHLBI/NIH HL078534 and NCI/NIH R1CA95393-01; DARPA, and UCSF Prostate Cancer SPORE award (NIH Grant P50 CA89520; and P01 CA072006), under Contract no. DE-AC02-05CH11231 awarded by the U.S. Department of Energy, at the University of California/Lawrence Berkeley National Laboratory.

REFERENCE TO SEQUENCE LISTING

The sequence listing in paper form is hereby incorporated by reference in its entirety as attached to the specification.

BACKGROUND OF THE INVENTION

1. Field of the Invention

The present invention relates to the fields of Surface Enhanced Raman Scattering (SERS) using a single and arrays of nanoplasmonic resonators for detection of enzymatic activity. The present invention relates specifically to the detection of protease activity, such as the Prostate Specific Antigen (PSA) and Proteolytically Active PSA for diagnostic applications in prostate cancer.

2. Related Art

Originally developed in 1928, Raman spectroscopy has been used extensively to characterize molecular properties (Kazuo Nakamoto John R. Ferraro, Chris W. Brown, *Introductory Raman Spectroscopy*, 2nd ed. (Elsevier Science, 2003). Surface-Enhanced Raman Spectroscopy (SERS) increases the Raman signal significantly (C. R. Yonzon, C. L. Haynes, X. Zhang et al., *Anal Chem* 76 (1), 78 (2004); A. E. Grow, L. L. Wood, J. L. Claycomb et al., *J Microbiol Methods* 53 (2), 221 (2003); K. Nithipatikom, M. J. McCoy, S. R. Hawi et al., *Anal Biochem* 322 (2), 198 (2003); J. B. Jackson and N. J. Halas, *P Natl Acad Sci USA* 101 (52), 17930 (2004)) through enhanced electromagnetic fields in close proximity to a surface. SERS measurements performed on rough metal surface or dispersed metal nanoparticle aggregates have shown the highest Raman enhancement factors up to $10^{14}$ for detection down to single molecule level (Katrin Kneipp, Harald Kneipp, Irving Itzkan et al., *Current Science (Bangalore)* 77 (7), 915 (1999); S. Nie and S. R. Emory, *Science* 275 (5303), 1102 (1997)) but these measurement often suffer from poor reproducibility (M. Moskovits, *Reviews of Modern Physics* 57 (3), 783 (1985)). To improve the reproducibility, other methods including self-assembly of metallic colloidal nano-particles (R. G. Freeman, K. C. Grabar, K. J. Allison et al., *Science* 267 (5204), 1629 (1995)), nanosphere lithography (NSL) and metal film over nanosphere (MFON) (C. L. Haynes and R. P. Van Duyne, *Journal of Physical Chemistry B* 107 (30), 7426 (2003)), electrochemical roughening of polished gold substrate (J. M. Sylvia, J. A. Janni, J. D. Klein et al., *Analytical Chemistry* 72 (23), 5834 (2000)), and periodic structured metallic substrate using electron-beam lithography (M. Kahl, E. Voges, S. Kostrewa et al., *Sensors and Actuators B-Chemical* 51 (1-3), 285 (1998)), have been developed to fabricate SERS substrate consisting homogeneous features over large area with reproducible enhancement factors up to $10^8$. Although these efforts lead to successful utilization of SERS analysis in many promising applications including gene and protein discrimination (Y. C. Cao, R. C. Jin, J. M. Nam et al., *J Am Chem Soc* 125 (48), 14676 (2003); Y. W. C. Cao, R. C. Jin, and C. A. Mirkin, *Science* 297 (5586), 1536 (2002); T. Vo-Dinh, F. Yan, and M. B. Wabuyele, *Journal of Raman Spectroscopy* 36 (6-7), 640 (2005)), bio-warfare agents detection (D. A. Stuart, K. B. Biggs, and R. P. Van Duyne, *Analyst* 131 (4), 568 (2006)) and real-time glucose monitoring (O. Lyandres, N. C. Shah, C. R. Yonzon et al., *Analytical Chemistry* 77 (19), 6134 (2005)), lacking of the ability to fabricate SERS hot-spots at specific location limits application for very small sample volume.

To overcome such limit, we recently developed tunable nanoplasmonic resonators (NPRs), consisting of thin $SiO_2$ layer sandwiched between metallic nano-disks described in Durant S. Su K, Steel M. J., Xiong Y. Sun C., Zhang X, *Journal of Physical Chemistry B* 110 (9), 3964 (2006) hereby incorporated by reference. The resonance frequency can be precisely tuned by varying the dielectric layer thickness and aspect-ratio of the NPRs. Individual NPRs can enhance the Raman intensity by a factor of $6.1 \times 10^{10}$; among the largest values obtained for a single SERS substrate or nanoparticle. Fabricated using well established nanolithography processes, the NPR-based method enables producing SERS hot-spots at desired location in a much smaller dimension reproducibly, allowing multiplexed high throughput detection and lab-on-chip applications.

Prostate cancer biomarker Prostate Specific Antigen (PSA), a kallikrein (hK) family serine protease (S. R. Denmeade and J. T. Isaacs, *BJU Int* 93 Suppl 1, 10 (2004); J. A. Clements, N. M. Willemsen, S. A. Myers et al., *Crit Rev Clin Lab Sci* 41 (3), 265 (2004)), is used as a model protease in the present application. The commonly used prostate-specific antigen (PSA) blood test has being widely used for early diagnosis and management of prostate cancer, the leading male cancer (H. Gronberg, *Lancet* 361 (9360), 859 (2003); S. R. Denmeade and J. T. Isaacs, *Nat Rev Cancer* 2 (5), 389 (2002)). However, serum PSA concentrations reflect the presence of benign prostatic hyperplasia (BPH) more often than cancer (A. Caplan and A. Kratz, *Am J Clin Pathol* 117 Suppl, S104 (2002); E. I. Canto, S. F. Shariat, and K. M. Slawin, *Curr Urol Rep* 5 (3), 203 (2004)). The lack of specificity causes a high false-positive rate and often leads to costly prostate needle biopsies for diagnosis and post-biopsy complications as well as considerable anxiety (M. B. Gretzer and A. W. Partin, *Urol Clin North Am* 30 (4), 677 (2003); A. Haese, M. Graefen, H. Huland et al., *Curr Urol Rep* 5 (3), 231 (2004)). Recent research has identified a family of highly specific peptides that can be cleaved by paPSA isoform in xenografts models (S. R. Denmeade, C. M. Jakobsen, S. Janssen et al., *J Natl Cancer Inst* 95 (13), 990 (2003)) and human samples (P. Wu, U. H. Stenman, M. Pakkala et al., *Prostate* 58 (4), 345 (2004); P. Wu, L. Zhu, U. H. Stenman et al., *Clin Chem* 50 (1), 125 (2004)) thus, measurement of paPSA protease activity from in vivo samples is possible and would be potentially valuable as a more specific screening agent for prostate cancer and in detection of recurrent disease.

However, reported results based on immunopeptidemetric assays (IMPA) exhibit low fluorescence signal-to-noise ratios, preventing reliable measurements at lower concentrations in the clinically important range of 60-300 pM (P. Wu, U. H. Stenman, M. Pakkala et al., *Prostate* 58 (4), 345 (2004); P. Wu, L. Zhu, U. H. Stenman et al., *Clin Chem* 50 (1), 125 (2004)). In addition, there is usually a limited number of prostate cancer cells (<1000) isolated from fine needle biopsy or circulating cell capture. No commercial method exists that can perform a paPSA protease activity assay on a small number of cells for clinical staging. Therefore, one goal of the present invention is to provide a method that allows specific and sensitive measurements of paPSA for prostate cancer detection in a very small sample volume.

BRIEF SUMMARY OF THE INVENTION

The present invention provides the detection and measurement of enzymatic activity in vitro and, in situ, using a nanosensor comprised of a nanoplasmonic resonator (NPR) with at least picomolar sensitivity. In one embodiment, a bioconjugated NPR enhances Raman spectra intensity in Surface-Enhanced Raman Spectroscopy (SERS) and enables sensitive single-step detection of enzymatic activity in extremely small volume.

In certain preferred embodiments, the invention provides a nanosensor, comprising a nanoplasmonic resonance SERS platform. The platform comprising a substrate featuring a surface enhanced Raman scattering (SERS) nanoplasmonic resonator singly or in an array, wherein the nanoplasmonic resonator (NPR) has a biomolecule conjugated thereto. In one embodiment, the NPR comprising metallic nanodisks with alternating shielding layer(s), having a tagged biomolecule conjugated or tethered to the surface of the NPR. In a preferred embodiment, the tag is a Raman active tag.

In one embodiment, the biomolecule is a peptide linked to a Raman active tag, wherein the peptide comprising a specific sequence that can be specifically modified or cleaved by an enzyme. Thus, this peptide-conjugated nanoplasmonic resonator is intended to be used as a specific screening tool to provide information on the presence, concentration and activity of enzymes such as proteases, kinases and peptidases. In one embodiment, the screen would measure activity of cancer biomarkers such as prostate-specific antigen (PSA) in a biological sample. In one embodiment, the peptides should be substrates specifically recognized, modified and/or acted on by the corresponding enzyme to be detected.

In another embodiment, real-time reaction monitoring also provides critical information on enzyme activity rather than just measuring the presence of the protein. Different Raman tag molecules may be used such that detection of two or more types of enzymes may be carried out by multiplexing peptide-conjugated NPRs. Furthermore, an array of the peptide-conjugated NPRs on a substrate is described for use to further amplify or expand detection.

In another embodiment, different biomolecule substrates orthogonal to each other, or with minor overlap in specificity, can be used to detect the corresponding enzyme. In one embodiment, a biomolecule library can be conjugated to the NPRs and spatially separated in either a random array or ordered microarray format. The multiplexed array of the biomolecule-nanoplasmonic resonators can be used to detect multiple enzymes simultaneously.

The NPR can also be manipulated by laser or magnetic fields to address at high accuracy spatially, so that it could be multiplexed as high density arrays (with sub-microliter volume). Additional spatial multiplexing for multiple proteases in a microarray or nanoarray format is contemplated. In addition, the magnetic or laser maneuverability allow biosensing at desired locations, which would be useful for obtaining in situ measurements intracellularly.

In another embodiment, the nanosensor herein described may be integrated into microfluidics system or other chip system. In one embodiment, the nanosensor-based assay can be performed in liquid phase, wherein the sample is contacted with the NPR nanosensor or the NPR array and the SERS measurements can be conducted.

DETAILED DESCRIPTION OF THE PREFERRED EMBODIMENT

Figure 1:
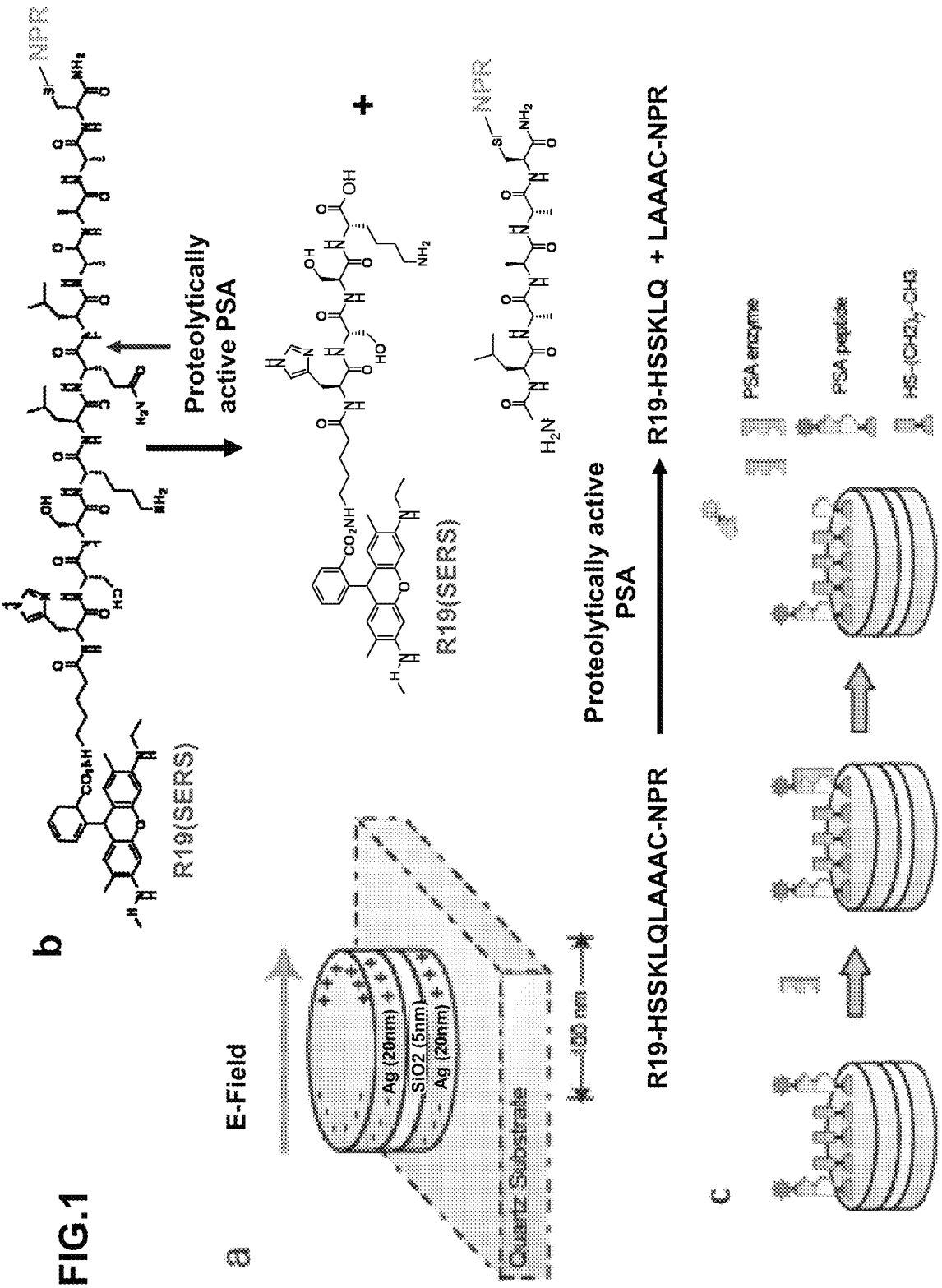
FIG. 1 Schematic illustration of the working principle of detecting PSA protease activity using peptide-conjugated NPR SERS nanosensors. (a) NPRs exhibit a tunable plasmon resonance and highly enhanced local electromagnetic field through coupled plasmonic resonance. NPRs with a short axis of 150 nm and long axis of 200 nm were made of multi-stacks of silver and $SiO_2$ layers with thicknesses of 25 nm and 5 nm, respectively. (b) The molecular structure of the biomarker that consists of Raman dye R19, PSA specific peptide sequence HSSKLQLAAAC (SEQ ID NO:1), and cysteine. The peptide can be cleaved by PSA enzyme between HSSKLQ and LAAAC. (c) The detection scheme of NPR functionalized with peptide sequence HSSKLQLAAAC (SEQ ID NO:1) and the Raman dye R19 (star). The presence of the PSA enzyme will cleave the peptide sequence. After cleavage, the diffusion of the R19 (star) away from the surface will be monitored by the loss of the SERS signatures of the R19 moiety. Packing molecule octanethiol ($HS-(CH_2)_2-CH_3$) was used to reduce the packing density of the reporting peptide on NPR surface, and thus, allows PSA enzyme to access the reporting peptide. (d) Optical microscopic image of NPRs arrays fabricated using standard e-beam lithography and thin film deposition process. Fabricated NPRS arrays consists of 30×30 NPRs with 500 nm spacing. Multiple NPRs arrays and alignment mark can be conveniently fabricated on the same substrate. (e) Magnified image of NPR array measured by Scanning Electron Microscope. Using precision lithography methods, the NPR can be prepared in a controlled manner. (f) Image of NPRs measured at higher magnification using Atomic Force Microscope (AFM). (g) Measured extinction spectrum of an NPR array at a wavelength range of 425 to 650 nm. The resonance peak of the NPR has been tuned to closely match the laser excitation and Raman emission frequencies, and thus, maximize the overall enhancement of the Raman signal. (h) Highly reproducible Raman spectra of para-mercaptoaniline (pMA) molecules conjugated on NPR surface measured at different NPRs arrays. Integration time is 30 seconds.
Figure 1:
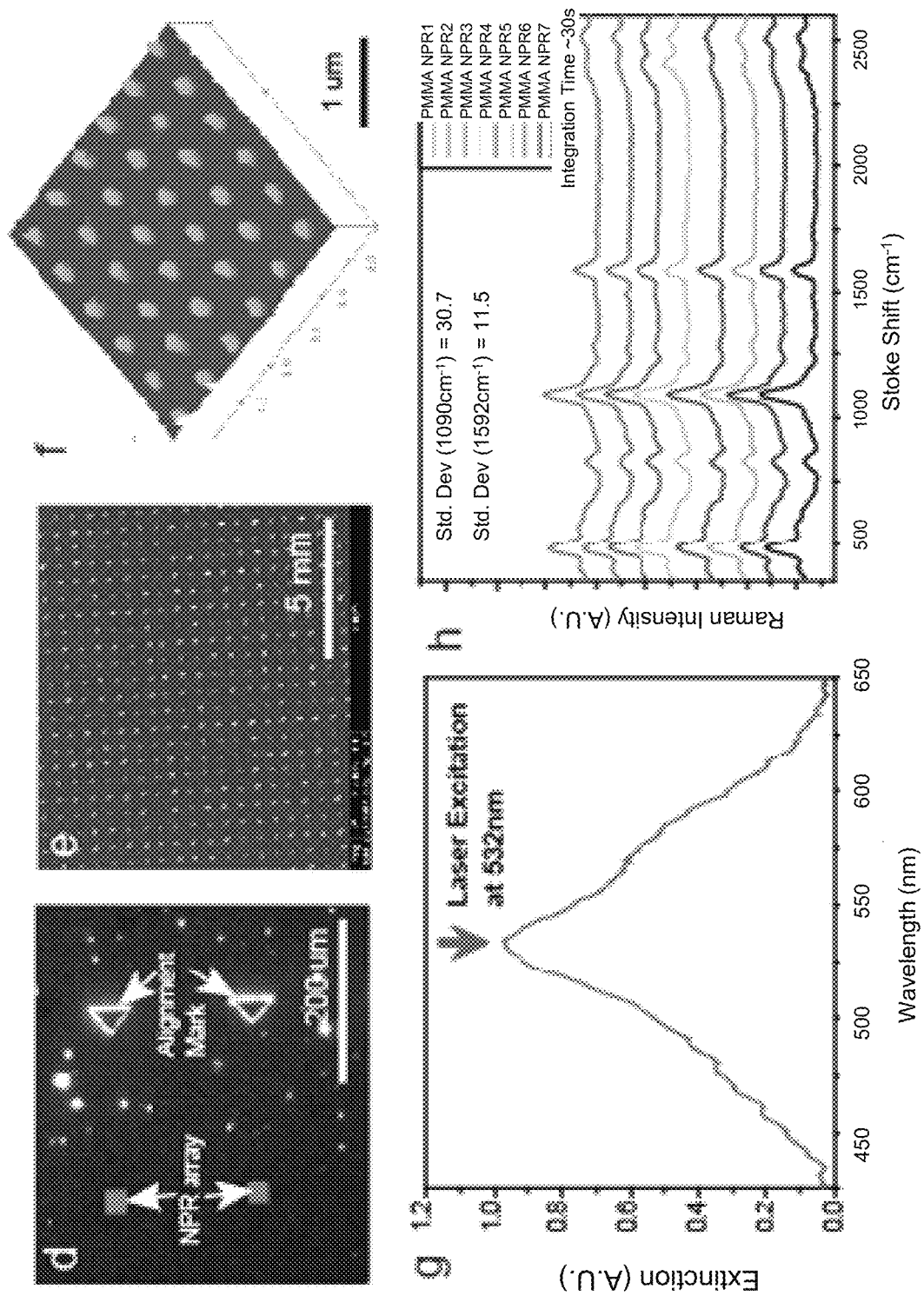

The present invention demonstrates the in vitro detection and measurement of enzymatic activity using a nanosensor comprised of a nanoplasmonic resonator (NPR) with at least picomolar sensitivity. In one embodiment, a bioconjugated NPR enhances Raman spectra intensity in Surface-Enhanced Raman Spectroscopy (SERS) and enables sensitive single-step detection of enzymatic activity in extremely small volume.

One of the major advantages and applications of the small volume property is that it is useful in detecting proteases such as prostate-specific antigen (PSA) activity of cancer cells at single cell level. The small volume requirement and sensitivity level makes it possible to detect PSA activity in captured circulating prostate cancer cells for indications of various disease states, e.g., metastasis, which is not feasible with conventional techniques. In semen, the PSA concentration is 10-150 μM, with approximately two thirds of the PSA enzymatically active. The sensitivity level achieved with the NPR PSA probe (nanomolar range) is sufficient for a seminal fluid based assay, thus the nanoplasmonic resonance SERS platform described herein is intended to have clinical applications.

In a preferred embodiment, the invention provides a nanosensor, comprising a nanoplasmonic resonance SERS platform. The platform comprising a substrate featuring a surface enhanced Raman scattering (SERS) nanoplasmonic resonator singly or in an array, wherein the nanoplasmonic resonator (NPR) has a biomolecule conjugated thereto. In one embodiment, the NPR comprising at least two nanodisks with an alternating thin shielding layer(s), and a tagged biomolecule conjugated or tethered to the surface of the NPR. In a preferred embodiment, the tag is a Raman active tag.

A variety of detection units of potential use in Raman spectroscopy are known in the art and any known Raman detection unit may be used. A non-limiting example of a Raman detection unit is disclosed in U.S. Pat. No. 6,002,471. In this example, the excitation beam is generated by either a Nd:YAG laser at 532 nm (nanometer) wavelength or a Ti:sapphire laser at 365 nm wavelength. Pulsed laser beams or continuous laser beams may be used. The excitation beam passes through confocal optics and a microscope objective, and may be focused onto a substrate containing attached biomolecule targets. Raman emission light target(s) can be collected by the microscope objective and the confocal optics, coupled to a monochromator for spectral dissociation. The confocal optics can include a combination of dichroic filters, barrier filters, confocal pinholes, lenses, and mirrors for reducing the background signal. Standard full field optics can be used as well as confocal optics.

The Raman emission signal can be detected by a Raman detector. The detector can include an avalanche photodiode interfaced with a computer for counting and digitization of the signal. Where arrays of target(s) are to be analyzed, the optical detection system may be designed to detect and localize Raman signals to specific locations on a chip or grid. For example, emitted light may be channeled to a CCD (charge coupled device) camera or other detector that is capable of simultaneously measuring light emission from 20 multiple pixels or groups of pixels within a detection field.

Various excitation sources include, but are not limited to, a nitrogen laser (Laser Science Inc.) at 337 nm and a helium-cadmium laser (Liconox) at 325 nm (U.S. Pat. No. 6,174, 677). The excitation beam can be spectrally purified with a bandpass filter 30 (Corion) and may be focused on a substrate 140 using a 6× objective lens (Newport, Model L6X). The objective lens can be used to both excite the indicator(s) and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) can be used to reduce Rayleigh scattered radiation. Alternative Raman detectors include, but are not limited to, an ISA HR-320 spectrograph equipped with a red-enhanced intensified charge-coupled device (RE-ICCD) detection system (Princeton Instruments). Other types of detectors may be used, such as charged injection devices, photodiode arrays or phototransistor arrays Referring now to FIG. 1A, the nanoscale dimension and the high local electromagnetic field enhancement of the NPR enables a high-sensitivity optical detection of biomolecular reactions on its surface. In a preferred embodiment, the nanoplasmonic resonators are lithographically defined metallodielectric nanoparticles comprising at least two nanodisks stacked vertically, separated by a shielding layer. In various embodiments, the NPR are preferably patterned on a substrate by electron beam lithography or other lithographic methods known in the art.

The substrate on which the NPRs are patterned can be comprised of quartz, polystyrene, silica, dextran, or any other materials with constant Raman spectra. In one embodiment, to prevent charging effects during the electron beam lithography, the substrate is further coated with a layer such as indium tin oxide. The layer can be sputtered, deposited coated or added using any other method onto the substrate to form a thin film. In another embodiment, the substrate is then spin-coated with a polymer to create a positive photoresist before exposure to create the patterns. In one embodiment, after exposure, patterns are developed using a solvent mixture, followed by multilayer electron beam evaporation and standard lift-off procedure.

In one embodiment, the NPRs are made as described in Example 1. In another embodiment, the NPRs are made as described in K. H. Su, Q. H. Wei, and X. Zhang, "Tunable and augmented plasmon resonances of Au/SiO$_2$/Au nanodisks", *Appl. Phys. Lett.* 88, 063118, 2006; and Kai-Hung Su, Stéphane Durant, Jennifer M. Steele, Yi Xiong, Cheng Sun, and Xiang Zhang, Raman Enhancement Factor of a Single Tunable Nanoplasmonic Resonator, *Journal of Physical Chemistry B*, 110 (9), 3964 (2006), both of which are hereby incorporated by reference in their entirety.

In a preferred embodiment, the nanoplasmonic resonator is comprised of nanodisks layered or stacked with an alternating shielding layer. For example, NPRs can be made having two nanodisks of gold with a shielding layer of $SiO_2$ sandwiched in between. In another embodiment, the two nanodisks of gold with a shielding layer of $SiO_2$ sandwiched in between is capped on one end with another shielding layer of $SiO_2$, thereby producing an $SiO_2/Au/SiO_2/Au$ nanoplasmonic resonator.

In one embodiment, the nanoscale layers are evaporated on the patterned substrate to form the nanodisk layers of the NPRs. In a preferred embodiment, each nanodisk is 50-500 nm at its widest point. The nanodisks can be comprised of a thin layer of a metal, a semiconductor material, multi-layers of metals, a metal oxide, an alloy, a polymer, or carbon nanomaterials. In certain embodiments the nanodisk(s) comprise a metal selected from the group consisting of Ga, Au, Ag, Cu, Al, Ta, Ti, Ru, Ir, Pt, Pd, Os, Mn, Hf, Zr, V, Nb, La, Y, Gd, Sr, Ba, Cs, Cr, Co, Ni, Zn, Ga, In, Cd, Rh, Re, W, Mo, and oxides, and/or alloys, and/or mixtures, and/or nitrides, and/or sintered matrix thereof.

Figure 6:
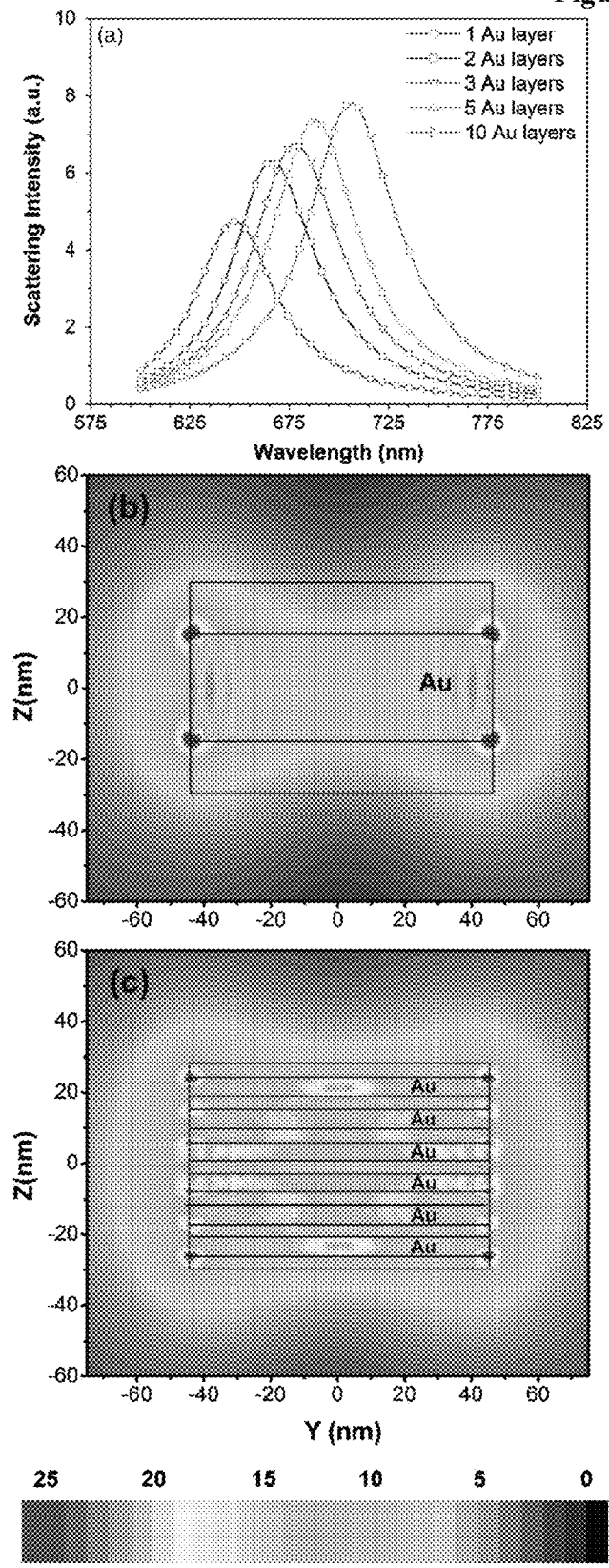
FIG. 6 (A) Simulated scattering spectra for single nanodisks with various metal layers. The nanodisk is circular with a 90 nm diameter, while the total thicknesses for metal layers and SiO$_2$ layers are kept both at 30 nm. The polarization of the incident light is polarized in the Y-axis direction. (B) Y-Z plane cross section of local electrical field distribution for the single Au layer nanodisk (SiO$_2$/Au/SiO$_2$) at the resonant frequency. (C) Y-Z plane cross section of local electrical field distribution for the 6 Au layer nanodisks (SiO2/Au)$^6$/SiO$_2$ at resonant frequency.

The shielding layer of material can be any material having a constant Raman spectra. The shielding layer functions as a tuning parameter for plasmon resonant frequency of the NPR. Compared to single layered metallic nanodisks, multilayered nanodisks exhibit several distinctive properties including significantly enhanced plasmon resonances and tunable resonance wavelengths which can be tailored to desired values by simply varying the dielectric layer thickness while the particle diameter is kept constant. Numerical calculations show that slicing one metal layer into metal multilayers leads to higher scattering intensity and more "hot spots," or regions of strong field enhancement. FIG. 6 shows a color simulated scattering spectra for nanodisks with various metal layers.

Thus, in another embodiment, each nanodisk layer in the NPR can be the same or different thickness. By choosing different layer thicknesses, the plasmon resonance wavelength and the surface enhancement factor can be tuned to match various applications. For instance, in Example 1, NPRs with a short axis of 150 nm and long axis of 200 nm were made of multi-stacks of silver and $SiO_2$ layers with thicknesses of 25 nm and 5 nm, respectively. Furthermore, by selective shielding of the outer surface of the metallic structure, the efficiency can be further enhanced by guiding the molecular assembly to the locations that exhibit strong electromagnetic fields. Thus, in another embodiment, the outer layers are shielding layers comprising material having a constant Raman spectra. FIG. 1A shows the schematics and transmission electron micrograph of a preferred nanoplasmonic resonator (NPR).

In one embodiment, the biomolecule is a peptide comprising a specific sequence that can be specifically cleaved by protease, linked to a Raman active tag.

A variety of Raman labels are known in the art (e.g., U.S. Pat. Nos. 5,306,403; 6,002,471; 6,174,677, which are incorporated herein by reference) and any such known Raman label(s) can be used. The labels typically have characteristic (e.g., unique) and highly visible/detectable optical signatures. Suitable Raman labels include, but are not limited to fluorophore, a chromophore, a quantum dot, a fluorescent microsphere, biotin, and the like. In certain embodiments the Raman label comprises a Rhodamine, a fluoresceine, or an exogenous chemical molecule. In certain embodiments the Raman label comprises a moiety acting as a Raman tag. Non-limiting examples of tag molecules include TRIT (tetramethyl rhodamine isothiol), NBC (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'tetrachlorofluorescein, 5-carboxyfluorescein, 5-carboxy rhodamine, 6-carboxyrhodamine, 6-10 carboxytetramethyl amino phthalocyanines, 6-carboxy-X-rhodamine, azomethines, cyanines, xanthines, succinylfluoresceins, aminoacridine, and cyanide (CN), thiol (SH), chlorine (el), bromine (Br), methyl, phorphorus (P), sulfur (S), SN, Al, Cd, Eu, Te, and compounds containing such moieties. In certain embodiments, carbon nanotubes, quantum dots (see, e.g., Evident Technologies, Troy N.Y.; Invitrogen/Molecular Probes, 15 etc.), or microspheres (e.g. fluorescent microspheres (see, e.g. Transfluosphres® from InvitrogenIMolecular Probes) can be used as Raman tags.

In various embodiments, one or more Raman labels (Raman tags) can be attached to the biomolecule (e.g., polypeptide) that is attached to the NPR(s). The presence of such Raman tags can enhance the change in Raman signal produced by cleavage of the peptide.

Thus, in one embodiment this Raman tagged biomolecule-conjugated nanoplasmonic resonator is intended to be used as a specific screening tool to provide information on the presence, concentration and enzymatic activity of enzymes and other cancer biomarkers, such as prostate-specific antigen (PSA) in a biological sample. In certain embodiments, the biomolecule is a peptide. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. In certain embodiments, multiple peptides are conjugated to the surface of the nanoscrescent, each being the same or different. In various embodiments approximately 5 to 500, more preferably about 10 to about 400, still more preferably about 20, 30, or 40 to about 200, 250, or 300, and most preferably about 50 to about 150 substrate molecules (e.g. peptides) are attached to the nanocrescent. In one embodiment, about 100 peptides are 15 conjugated to the nanocrescent with direct reaction between Au and the thiol group on the Peptide.

The enzyme whose activity is being monitored can include but is not limited to, an enzyme, protease, kinase, peptidase or other biological molecule. In various embodiments, the biomolecules are peptides specifically recognized and modified or cleaved by the corresponding enzyme to be detected. In another embodiment, the biomolecules are peptides specifically recognized and phosphorylated by the kinase to be detected. Various types of proteases and peptides specifically recognized by those proteases are also described in co-pending International Application No. PCT/US2007/010722, entitled "Detection of Protease and Protease Activity Using a Single Nanoscrescent SERS Probe." Related methods using a nanocrescent probe for SERS detection of a protease or other biomolecules is also described in PCT/US2007/010722, which is hereby incorporated by reference for all purposes.

In a preferred embodiment, the biomolecule is a peptide, wherein the peptide is an oligopeptide about 10-12 amino acid residues in length. However, the peptide can be as short as 4 amino acid residues, and as long as 100 amino acids. In one embodiment, the peptides should be sequences specifically recognized and modified by a corresponding enzyme. The peptide can be synthesized and obtained commercially or the peptides can be made according to the methods described in Example 1. Raman active molecules such as biotin or Rhodamine 6G (R19) (FIG. 1B) are preferably grafted through a short polyethyleneglycol or aminovaleric acid linker at the amino terminus of the peptide.

The biomolecules may be "conjugated" (i.e., linked) to the nanoplasmonic resonator directly or via one or more linking agents. "Linking agent" as used herein refers to any compound that forms a bond between the NPR and the biomolecule and include e.g., a functional group, an affinity agent, or a stabilizing group. Suitable bonds include ionic interactions, covalent chemical bonds, physical forces such van der Waals or hydrophobic interactions, encapsulation, embedding, binding affinity, attraction or recognition, and various types of primary, secondary, tertiary linkages including but not limited to, peptide, ether, ester, acryl, aldehyde, ketone, acryloyl, thiol, carboxyl, hydroxyl, sulfhydryl and amine linkages or the like.

In one embodiment, hundreds of peptides are conjugated to the NPR with direct reaction between the metallic nanodisk of the NPR and a thiol group on the peptide. In another embodiment, the NPR metallic surface can also be modified with either amine or carboxyl group so the peptide can be tethered through peptide bond on the NPR surface, via reaction with a heterobifunctional crosslinker that can react with both amine group and thiol group, or carboxyl group and thiol group. In a specific embodiment, an Au/SiO$_2$/Au/SiO$_2$ NPR can be functionalized with amine or carboxyl functional groups, and the peptides can be crosslinked via the crosslinker to the amine and carboxyl functional groups. Various crosslinkers can be used for the conjugation of thiol-activated peptides, and the surface functional groups on the NPRs, such as amine, carboxyl, and hydroxyl groups.

In one preferred embodiment, the substrate peptide is tethered onto the surface of an Au/SiO$_2$/Au NPR using a cysteine group at the carboxyl terminus of the peptide to attach the peptide to the Au surface, relying on the Au-thiol reaction to form a covalent bond. In a preferred embodiment, multiple peptides are similarly conjugated to the surface of the NPR, each being the same or different.

The NPR indicators described herein can utilize polypeptide sequences comprising one or more recognition site(s) for any protease(s) it is desired to detect. Proteases (proteolytic activity) are not only required for maintenance of normal cellular functions but are also central to the pathogenesis of a variety of human diseases. Parasitic (for example schistosomiasis and malaria), fungal (such as *C. albicans*) and viral infections (for example HIV, herpes and hepatitis), and also cancer, inflammatory, respiratory, cardiovascular and neurodegenerative diseases, including Alzheimer's, require proteolytic activity for progress. Detection of protease presence, quantity, or activity is thus useful as a diagnostic/prognostic marker for the presence or likelihood of disease. In addition, detection of protease activity (or the inhibition thereof) is useful in screening for protease inhibitor therapeutics for the treatment of a number of pathologies.

A "protease" that can be detected and/or quantified according to the invention is an enzyme that typically hydrolyzes a peptide bond between a pair of amino 20 acids located in a polypeptide chain, also called an endoprotease. Proteases are typically defined by reference to the nucleophile in the catalytic center of the enzyme. The most common nucleophiles arise from the side chains of serine, aspartic acid, and cysteine, resulting in families of proteases, such as serine proteases (Paetzel et al. (1997) *Trends Biochem. Sci.* 22: 28-31), aspartyl proteases (Spinelli et al. (1991) *Biochemie* 73: 1391-25 1396), and cysteine proteases (Altschuh et al. (1994) *Prot. Eng.* 7: 769-75, 1994). Metalloproteases usually contain a zinc catalytic metal ion at the catalytic site (Klimpel et al. (1994) *Mol. Microbiol.* 13: 1093-1100).

A "protease recognition site" is a contiguous sequence of amino acids connected by peptide bonds that contains a pair of amino acids which is connected by a peptide bond that is hydrolyzed by a particular protease. Optionally, a protease recognition site can include one or more amino acids on either side of the peptide bond to be hydrolyzed, to which the catalytic site of the protease also binds (Schecter and Berger, (1967) *Biochem. Biophys. Res. Commun.* 27: 157-62), or the recognition site and cleavage site on the protease substrate can be two different sites that are separated by one or more (e.g., two to four) amino acids.

The specific sequence of amino acids in the protease recognition site typically depends on the catalytic mechanism of the protease, which is defined by the nature of the functional group at the protease's active site. For example, trypsin hydrolyzes peptide bonds whose carbonyl function is donated by either a lysine or an arginine residue, regardless of the length or amino acid sequence of the polypeptide chain. Factor Xa, however, recognizes the specific sequence Ile-Glu-Gly-Arg and hydrolyzes peptide bonds on the C-terminal side of the Arg. Various preferred protease recognition sites include, but are not limited to protease recognition sites for proteases from the serine protease family, or for metalloproteases, or for a protease from the cysteine protease family, and/or the aspartic acid protease family, and/or the glutamic acid protease family. In certain embodiments preferred serine proteases recognition sites include, but are not limited to recognition sites for chymotrypsin-like proteases, and/or subtilisin-like proteases, and/or alpha/beta hydrolases, and/or signal peptidases. In certain embodiments preferred metalloprotease recognition sites include, but are not limited to recognition sites for metallocarboxypeptidases or metalloendopeptidases. Illustrative proteases and protease recognition sites are shown below in Table 1.

TABLE 1

Illustrative proteases and protease recognition sites (* indicates the peptide bond being hydrolyzed).

| Protease Family | Protease | Protease Recognition Sites |
|---|---|---|
| serine | factor Xa | Ile-Gly-Gly-Arg* |
| serine | trypsin | Lys*, Arg* |
| serine | chymotrypsin | Tyr*, Phe*, Leu*, Ile*, Val*, Trp*, and His* at high pH |
| serine | thrombin | Arg* |
| serine | PSA | |
| serine and cysteine variants | peanut mottle polyvirus Nla protease | Glul-Xaa-Xaa-Tyr-Gln*(Ser/Gly) |
| cysteine | papaine | Arg*, Lys*, Phe* |
| cysteine | bromelaine | Lys*, Ala*, Tyr*, Gly* |
| cysteine | cathepsin B | Arg*Arg, Phe*Arg |
| cysteine | cathepsin L | Phe*Arg |
| aspartyl | HIV protease | Phe*Pro |
| aspartyl | *S. cerevisiae* yapsin 2 | Lys*, Arg* |
| aspartyl | cathepsin D | Phe*Phe Phe*Lys Leu*Phe Leu*Tyr |
| metallo- | thermolysin | *Tyr, *Phe, *Leu, *Ile, *Val, Trp, and *His |
| metallo- | peptidyl-Lys metalloendopeptidase | Xaa*Lys |

TABLE 1-continued

Illustrative proteases and protease recognition sites (* indicates the peptide bond being hydrolyzed).

| Protease Family | Protease | Protease Recognition Sites |
|---|---|---|
| metallo- | peptidyl-Asp metallodndopeptidase | Xaa*Asp<br>Xaa*Glu<br>Xaa*Cys |
| metallo- | coccolysin | *Leu, *Phe, *Tyr, *Ala |
| metallo- | autolysin | Leu-Trp-Met*Arg-Phe-Ala |
| metallo- | gelatinase A (MMP-2) | Pro-Gln-Gly*Ile-Ala-Gly-Gln |
| metallo- | human neutrophil collagenase (MMP-8) | Gly-Leu-Ser-Ser-Asn-Pro*Ile-Gln-Pro |

In a specific embodiment to detect PSA, the peptide design will follow the amino acid sequence of the active site of PSA-specific peptides with serine residues and flanking sequences that can be recognized by PSA. In a preferred embodiment, the peptide contains the sequence of HSSKLQ-LAAAC (SEQ ID NO:1) which has been shown to have very high specificity for proteolytically active PSA. (See Denmeade, S. R. et al. Specific and efficient peptide substrates for assaying the proteolytic activity of prostate-specific antigen. *Cancer Res* 57, 4924-4930 (1997)). It has been shown that HSSKLQ-L is cleaved by PSA but not by any other proteases in vivo in a mouse model. Thus, in another embodiment, multiple peptides can be generated, each having a random or known sequence portion, so long as each incorporates the highly specific sequence of HSSKLQ-LAAAC (SEQ ID NO:1).

The PSA digestion site is between the Glutamine (Q) and Leucine (L) residues in the peptide HSSKLQ-LAAAC (SEQ ID NO:1), and the peptides are digested into 2 fragments, HSSKLQ and LAAAC. In the present preferred embodiment, the peptide is preferably tethered to the NPR surface as shown in FIG. 1B, such that the PSA peptide is not sterically hindered from the PSA enzyme and thereby optimally accessible, and the Raman tag, R19, is attached to the peptide at the Histidine. It is contemplated that an additional spacer synthesized in between the peptide sequence HSSKLQ-LAAAC (SEQ ID NO:1) and the NPR after the Cys (C) residue, will improve the presentation of PSA substrate peptide HSSKLQ on the surface and thereby increase the detection sensitivity. Although by doing so the distance of the Raman tag molecules could be farther from the NPR surface and resulting in lower Raman intensity level because the coil-like short peptide structure implies large chance for the distal Raman tag molecule to contact the metal surface of the NPR. In a preferred embodiment, the spacer is a packing molecule such as octanethiol (HS—$(CH_2)_2$—$CH_3$) and used to reduce the packing density of the reporting peptide on NPR surface, and thus, allows the enzyme access to the reporting peptide.

The present approach can be used to detect the presence of other hydrolytic biological molecules. Thus, for example the peptide protease substrate can be replaced with single or double-stranded nucleic acids (RNA or DNA), and the indicator can detect and/or quantify the presence of active nucleases. In such instances, the nucleic acid substrate will typically comprise one or 30 more recognition sites for nucleases (e.g. restriction endonucleases). The nuclease recognition sites typically range in length from about 3 bp, 4 bp, 5 bp, 6 bp, 7 bp, 8 bp, 9 bp or 10 bp to about 15 bp, 20 bp, 25 bp, or 30 bp. In various embodiments the nucleic acid can range in length from about 3 bp to about 200 bp, preferably from about 4 bp to about 100 bp, more preferably from about 6, 8, 10, 16, or 20 bp to about 80, 60, 40, or 30 bp.

In another embodiment, essentially any molecule that can be phosphorylated by a kinase can be used as a kinase substrate in the methods and compositions described herein. While proteins/peptides comprise the largest substrate class for kinases, a number of other kinase substrates are known as well. Such substrates include, but are not limited to various sugars (e.g., hexose, gluclose, fructose, mannose, etc.), nucleotides/nucleic acids, acetate, butyrate, fatty acids, sphinganine, diacylglycerol, ceramide, and the like. Illustrative protein kinase substrates and the sequences is described in the sequence listing and Table 3.

TABLE 3

Illustrative protein kinase substrates.

| Kinase | Substrate | SEQ ID NO |
|---|---|---|
| cAMP-dependent protein kinase | LRRASLG (Kemptide) | 2 |
| cAMP dependent protein kinase (PKA) | GRTGRRNSI | 3 |
| protein kinase C (PKC) | QKRPSQRSKYL | 4 |
| protein kinase Akt/PKB | RPRAATF | 5 |
| Abl kinase | EAIYAAPFAKKK | 6 |
| 5'-AMP-activated protein kinase (AMPK) | HMRSAMSGLHLVKRR | 7 |
| Ca2+/calmodulin-dependent protein kinase | KKALRRQETVDAL (Autocamtide-2) | 8 |
| cyclin-dependent kinase 2 (cdc2) | (Ac-S)PGRRRRK | 9 |
| cyclin-dependent kinase 2 (Cdk2) | HHASPRK | 10 |
| cyclin-dependent kinase 5 (Cdk5) | PKTPKKAKKL | 11 |

TABLE 3-continued

Illustrative protein kinase substrates.

| Kinase | Substrate | SEQ ID NO |
|---|---|---|
| casein kinase 1 (CK1) | RRKDLHDDEEDEAMSITA | 12 |
| CK2 alpha subunit or holoenzyme | RRRDDDSDDD | 13 |
| DYRK family protein kinases | KKISGRLSPIMTEQ | 14 |
| GSK3 alpha and beta | YRRAAVPPSPSLSRHSSPHQ(pS)EDEEE | 15 |
| Src kinase | KVEKIGEGTYGVVYK | 16 |
| checkpoint kinases CHK1 and CHK2 | KKKVSRSGLYRSPSMPENLNRPR | 17 |
| protein tyrosine kinases (PTKs) in phosphorylation assays. | Poly(Glu:Tyr)$_{4:1}$ is sodium salt polymer with a random amino acid distribution and a molar ratio of 4:1 for glutamic acid:tyrosine | |

Thus, for example, a protein, and/or sugar, and/or complex carbohydrate, and/or lipid, and/or nucleic acid "substrate" can be provided coupled to one or more NPRs when the substrate is recognized and bound by a cognate binding partner, the Raman spectrum will be changed and the interaction is detected.

A typical experimental system configuration is shown in FIG. 6, comprising a microscopy system with Raman spectrometer used to acquire Raman scattering spectra from single tagged nanoplasmonic resonators. In a preferred embodiment, the system is comprised of inverted microscope equipped with a digital camera and a monochromator with a spectrograph CCD camera, a laser source and an optical lens. In one embodiment, Raman spectra can be measured using a modified inverted microscope, such as the Carl Zeiss Axiovert 200 (Carl Zeiss, Germany), with a 50× objective in a backscattering configuration. The laser wavelength can be in the visible and near infrared region. In a preferred embodiment, a 785 nm semiconductor laser is used as the excitation source of Raman scattering, and the laser beam is focused by a 40× objective lens on the NPR. The 785 nm or other near infrared light source can assure less absorption by the biological tissue and lower fluorescence background. However, for certain applications, lower wavelength excitation light might be more advantageous, and even UV light excitation can be used for applications. The excitation power can also be measured by a photometer to insure an output of ~0.5 to 1.0 mW. The Raman scattering light is then collected through the same optical pathway through a long-pass filter and analyzed by the spectrometer. The Raman spectrometer is preferably linked to a computer whereby the spectrometer can be controlled and the spectra can be obtained and a spectrograph can be observed. The spectral detection can be done with ordinary spectral polychrometer and cooled CCD camera. The monitored wavenumbers of Raman peaks range from 400 cm$^{-1}$ to 2000 cm$^{-1}$.

In one embodiment, the peptide-conjugated NPRs are incubated with a sample suspected of containing the biomolecule to be detected, preferably in a closed transparent microchamber. The microchamber is mounted on a 37° C. thermal plate on an inverted Raman microscope with darkfield illumination for nanoparticle visualization. The NPRs are visualized using the darkfield illumination from oblique angles as the bright dots shown in the inset pictures in FIG. 1D. The excitation laser is focused on the NPRs by a microscopy objective lens. The SERS signal is collected by the same objective lens and analyzed by a spectrometer. The pictures in FIG. 1D show the ~0.8 mW excitation laser spot focusing on a field of NPRs.

The real-time detection of enzymatic reactions can occur within 30 minutes. However, the incubation and detection can be as short as 1 to 5 minutes and as long as 24 hours, or longer, if the application needs longer incubation time biologically. After initial centrifugal fractionation, the soluble content in biological sample can be directly incubated with the NPRs or the NPR array. In one embodiment, to specifically inhibit the protease-mediated proteolysis of the conjugated peptides, protease inhibitors are introduced prior to the addition of the protease. For example, the peptide digestion by PSA is more than 90% suppressed after the addition of inhibitors given the same experimental conditions.

In various embodiments the enzyme presence, and/or concentration, and/or activity is determined in a biological sample. The biological sample can include essentially any biomaterial that it is desired to assay. Such biomaterials include, but are not limited to biofluids such as blood or blood fractions, lymph, cerebrospinal fluid, seminal fluid, urine, oral fluid and the like, tissue samples, cell samples, tissue or organ biopsies or aspirates, histological specimens, and the like.

One typical experimental detection scheme for enzyme presence, concentration and activity is shown in FIG. 5. In the method, a solution or sample is provided to a peptide-conjugated SERS NPR or NPR array. Before the enzymatic reaction, the SERS spectrum of a peptide-conjugated NPR contains the characteristic peaks from the Raman tag molecules, the peptides, and the nanoplasmonic resonator. The enzymatic reaction by the enzyme should modify the peptide at a predetermined modification site. For example, during the digestion reaction by PSA, the peptide HSSKLQ-L is cleaved between the Q and L residues, here denoted by a dashed line. The SERS spectra of the artificial peptides change after cleavage by the protease because the cleavage fragment containing the Raman tag molecules diffuses away from the NPR surface, while the other fragment remains on the NPR surface. The characteristic SERS peaks of the molecular moieties with the Raman active tag disappear due to the diffusive dislocation of the tag molecules from the NPR surface into the solution after peptide digestion; therefore the existence and concentration of the proteolytically active PSA in solution can be probed by monitoring the SERS spectra of the peptide-conjugated NPRs. The Raman scattering signal of the attached peptide is then amplified by the NPR and detected by a microscopy system as described comprising a Raman spectrometer to acquire Raman scattering spectra from single or arrayed NPRs. For example, as shown in FIG. 1g, the measured resonance peak of NPRs-peptide-R19 conjugates closely matches laser excitation wavelength at 532 nm and thus, maximizes the enhancement of Raman scattering. As shown in FIG. 1h, NPR-based SERS substrate exhibits reproducible Raman spectrum with consistent enhancement factor at same order of magnitude. The variation of experimentally measured the SERS intensities obtained from 6 different NPR array are below 25% and it can be easily normalized in the experiment.

The reaction dynamics can be monitored by time-resolved SERS spectra acquisitions. In one embodiment, the assay can be performed by exposing the biomolecule-conjugated NPR array to biological fluidic samples and the subsequent time-dependent R19 Raman spectra change is recorded at an interval of about one minute and an integration time of about 30 seconds. The Raman peak at 1316 $cm^{-1}$ of SERS label molecule (R19) can be monitored as the primary signature peak, while the other signature peaks such as 1456 $cm^{-1}$, 1526 $cm^{-1}$, and 1597 $cm^{-1}$ peaks, may be also monitored as additional references (see FIG. 2). The time-resolved spectral measurement in the presence of an enzyme can be plotted as in FIG. 2c. The SERS intensities are proportional to any remaining biomolecules on the NPR surface that have not been acted on by the enzyme, thus making the normalized SERS intensity change a direct indicator of enzyme activity. Despite the variation in the initial intensity of different Raman signature peaks, the normalized data all converge into the same curve, indicating the normalized SERS intensity change is a reliable measure to quantitatively determine the peptide being profiled or detected.

For example, as shown in FIG. 2c, before enzyme addition, the peptide-conjugated NPR shows steady intensities for all the peaks over a 10 minute period. However, upon addition of an enzyme, a significant decrease in each Raman peak is observed in the first 10-12 minutes, indicating that the enzyme is active and was able to cleave the peptides on the NPR. At the endpoint of 30 minutes, the decrease of the Raman signal reaches a plateau at PSA concentration of 6 nM while at lower concentration level (~pM), the signal continues to decrease at a much lower rate. Another serine protease, Granzyme B, was selected as a negative control (FIG. 2b-c). Within 50 minutes of recording, no substantial changes in SERS intensity was observed, even at concentrations up to 1 μM. This result demonstrates that the decrease of Raman signal in the PSA assay was based on a genuine enzymatic process, rather than a non-specific hydrolysis reaction or due to the displacement of the peptide from the surface by other components in the buffer In a preferred embodiment, the time-lapse intensities of the Raman peak of the Raman active tag in the NPR SERS probe in the digestion reaction is obtained with the protease, the protease with inhibitor, and a negative control, respectively. All the peak intensity values are normalized to the internal control peak (e.g., In FIG. 1g, the peak intensity measured for the R19-peptide and NPR is 532 $cm^{-1}$) and the initial peak intensity at the wavenumber of either the positive or negative control. In one embodiment, the negative control is a NPR-peptide hybrid, in which the peptide is not a substrate of the protease(s) of interest and would not be cleaved by the protease(s) being studied. The results should indicate that the peptides are efficiently and specifically cleaved by PSA by the gradual disappearance of the peak intensity of the Raman active tag.

The NPR particle serves as the Raman signal amplifier and the detected Raman signal comes from all the peptides tethered on the surface of the NPR particle. In one embodiment, at least 100 peptide molecules are attached per NPR. Even if this number of peptides is attached, it is contemplated that the NPR surface with the highest SERS signal is not fully taken advantage of, if a small percentage of the peptides are attached to the region that provides the greatest enhancement in electromagnetic field (FIG. 1C). The numerical simulation (FIG. 1c) indicates the amplitude of the local electric field can be enhanced by close to 20 dB (100 fold) especially around the edge of the nanodisk. Due to the fourth power relation between the electric field amplitude and the Raman enhancement factor, the peptide Raman signal could be amplified several fold (e.g. $10^8$) by the NPR.

Furthermore, because tens to hundreds of peptides are used in the conjugation reaction for each NPR on average, the disappearance of the characteristic Raman peaks from the tag molecules is not abrupt. Since most of the enhanced field is concentrated around the tip area, which accounts for ~⅙ of total area of the NPR, the actual molecule number contributing to the Raman scattering signal in this high enhancement area is less than 20, even if assuming the conjugation efficiency is 100% (FIG. 1d).

In a preferred embodiment, a positive control is used. For example, in one embodiment, the intensities of the Raman peak for a positive control as a function of PSA digestion time for various PSA concentrations are obtained before detection of PSA presence or activity in a sample. The typical SERS spectra of the peptide-conjugated NPRs with positive controls biotin and R19 Raman tag molecules are shown in FIGS. 3a and 3b, respectively. By comparing the SERS spectra before and 2 hours after the peptide digestion experiments, the Raman peaks from the NPR core (e.g., polystyrene core, e.g. 1003 $cm^{-1}$) remain constant, and thus can also serve as an internal control. The digestion rate is related to the PSA concentration and PSA activity is typically observed in 30 min for a concentration 1 nM (with ~50% reduction in biotin signal intensity, data not shown). Some Raman peaks from the partial amino acid chain remaining on the NPR surface after digestion may still appear in the spectra, although the peak positions have slight changes and the peak intensities decrease due to possible conformational changes upon peptide cleavage.

In another embodiment, a negative control is run to show that the peptides are specifically cleaved by protease present in the sample. Example 1 shows the specificity of the conjugated peptides to PSA using other serine proteases such as Granzyme B, which can serve as a negative control. FIGS. 2B and 2C shows the time-lapse SERS spectra of NPRs with R19 tag molecules in the two control experiments with the PSA inhibitor and the serine protease Granzyme B, which has orthogonal substrate specificity to PSA, respectively. In the control experiment of peptide digestion by 420 nM Granzyme B, the reaction rate showed no statistically significant difference from the inhibitor-treated reaction. The inability for Granzyme B to cleave the peptide is also expected as PSA has been shown to be the only protease for the HSSKLQ-LAAAC sequence in vivo.

In a preferred embodiment, this peptide-conjugated NPR can be used as a specific screening tool to provide information on the concentration and proteolytic activity of the cancer biomarker PSA in biological samples obtained from patients in a clinical setting.

In another embodiment, the peptide-conjugated NPR can be used as a specific screening tool to provide information on the concentration and enzymatic activity of a biomarker, enzyme, kinase or other protease in biological samples obtained from patients in a clinical setting.

It is contemplated that one application of the present probes is the incorporation of an NPR particle into a microfluidic device which can automate and facilitate sample delivery and washing process. The NPR particles can be also delivered in real-time or immobilized in the device.

In another embodiment, NPRs can be spatially arranged in a microarray format to achieve multiplexed measurements with broad applications, by measuring all known proteases in unprocessed biological samples without complex sample processing and purification steps. The multiplexity of the substrate peptide spatially can be achieved with a microarrayer with industry standard protocols, when combined with NPR nanoarray clusters arranged in microarray format. Even if each of the 500+ proteases are cross-interrogated by 10 different substrate peptides, the array still has an easily manageable feature number of less than ten thousand.

EXAMPLE 1

Raman Enhancement Factor of a Single Tunable Nanoplasmonic Resonator (TNPR)

The TNPRs were patterned on quartz substrates (HOYA Co.) by electron beam lithography (EBL) (Leica Microsystems Nanowriter Series EBL 100). A 30 nm thick indium tin oxide (ITO) layer was first sputtered on the substrate to prevent charging effects during the EBL process. Poly(methyl methacrylate) (100 nm thick, MicroChem. Corp. PMMA) films, spincoated on the ITO-quartz glass, were used as a positive photoresist. After exposure, the patterns were developed using a 1:3 ratio of a methyl isobutyl ketone and isopropyl alcohol mixture, followed by multilayer electron beam evaporation of silver and oxide and standard lift-off procedures. We fabricated three-layered $Ag/SiO_2/Ag$ and four-layered $Ag/SiO_2/Ag/SiO_2$ TNPRs on the same substrate (we refer to the four-layered TNPR as the capped TNPR in this example), with each silver and $SiO_2$ layer thickness fixed at 20 and 5 nm, respectively. A shadow mask was inserted over the three-layered TNPRs during deposition of the additional 5 nm $SiO_2$ capping layer to prevent deposition on the three-layered TNPRs. The samples were measured by scanning electron microscopy and atomic force microscopy to determine their sizes, shapes, and thicknesses. The SiO2 layer sandwiched between the metallic layers can be used to tune the surface plasmon resonance frequency by adjusting its thickness. The EF can be maximized by matching the surface plasmon resonance to the pump laser frequency. Under an optical microscope, these particles, as shown in FIG. 1d, are distinctively visible due to the strong scattering of light at resonant wavelengths. Scanning electron microscopy (SEM) images (FIG. 1e) show that the TNPRs are slightly elongated with a long axis and short axis of 117 and 81 nm, respectively. Atomic force microscopy (AFM) measurement (FIG. 1f) confirms that the height difference between capped TNPRs and noncapped TNPRs is 5 nm, which matches the thickness of the SiO2 capping layer. Conducting AFM was used to ensure a good $SiO_2$ layer coverage between the metal disks.

Scattering spectra were obtained by illuminating the TNPRs with collimated light delivered by a multimode optical fiber from a 150 W Xe white light source. The light was delivered through a right angle prism at an angle resulting in total internal reflection (TIR), and the scattered light was collected with a JY (550 grating) spectrometer system (Jobin Yvon). See FIG. 5B. For the SERS experiment, SERS spectra were measured using a modified Zeiss inverted confocal microscope with a 20× objective in a backscattering geometry. An argon laser operating at 514 nm (attenuated to ~10 mW) was coupled into the microscope, and the appropriate interference filters and holographic notch filter (Kaiser) were placed in the beam path to remove the unwanted laser lines. The output light path was coupled into the same spectroscope as the scattering spectra measurement. See FIG. 5A.

In the measurements, the polarization of the incident E-field is parallel to the TNPR long axis. FIG. 2a depicts the scattering spectra of an individual TNPR and a capped TNPR with resonant peaks at 516 and 536 nm, respectively. The sandwiched $SiO_2$ layer works as a tunable coupling factor for the plasmon resonant frequency, and the top $SiO_2$ layer works as a cover layer to prevent the molecules from self-assembling on top of the metal surface. The observed red-shift of the resonance spectrum of the capped TNPR is due to the presence of the $SiO_2$ layer, which locally increases the refractive index. 17 p-Mercaptoaniline (pMA), a commonly used Raman dye, was selected in this study. The low fluorescence emission background makes it a good candidate for qualitative analysis of the Raman signal.

To ensure maximum coverage of the pMA monolayer on the TNPR surface, the substrates were incubated in a 100 iM pMA solution for more than 24 h. After repeatedly rinsing with DI water to remove unwanted pMA adsorbed on the substrate and $SiO_2$ capping layer, the substrate was thoroughly dried with N2 gas. The spectra measurements indicate the scattering peak positions of pMA-coated capped and noncapped TNPRs were shifted to 534 and 550 nm, respectively (FIG. 2b). The results indicate that the presence of pMA in the vicinity of the TNPR causes a red-shift of the resonance spectrum, equaling 18 nm for noncapped TNPRs and 14 nm for capped TNPRs. This observation shows that pMA on top of an uncapped TNPR does not lead to a significant shift (below 5 nm) and the surface plasmon modes in the TNPR may be more sensitive to the local refractive index change on the sidewall (in the direction of the excitation electric field) than on the top surface. Numerical simulations are more desirable to obtain a qualitative explanation of the peak shift for different sample configurations. It should be noted that these peak shifts suggest TNPRs can also serve as molecule/bio sensors to monitor local refractive index changes.

Figure 3:
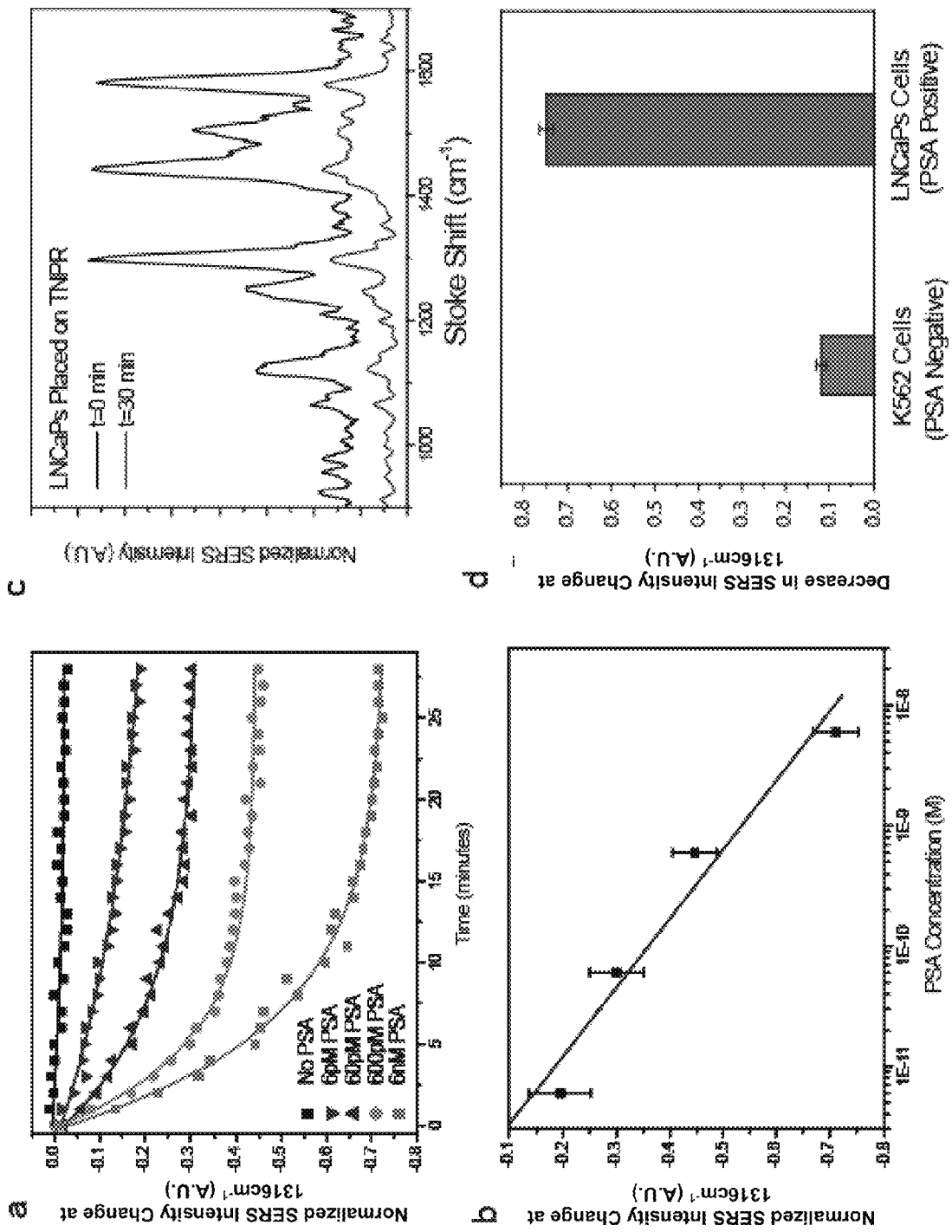
FIG. 3 Time-resolved measurements of PSA activity by varying the active PSA concentration. (a) Normalized SERS intensity change for 1316 $cm^{-1}$ peak at active PSA concentration from 6 pM to 6 nM. The decreasing of SERS intensity can be clearly measured while no significant change can be observed in the control experiment with no active PSA protease. (b) Concentration dependence of normalized SERS intensity change obtained at 30 min. (c) Protease activity measurement obtained from unprocessed extracellular fluid (ECF): Raman spectra obtained at the beginning of exposing LNCaP cells (positive control) ECF to NPR nanosensors (t=0 min) and after 30 minutes. (d) Normalized change of SERS intensity at 1316 cm$^{-1}$ peak indicating PSA proteolytic activity in the fluid extracted from LNCaP and K562 cell lines.

The SERS EF for the TNPRs was evaluated by directly comparing the SERS intensity obtained from TNPRs with unenhanced molecules using the expression EF) $(RS^{TNPR}/RS^{reference})([reference]/[TNPR])$. $RS^{TNPR}$ and $RS^{reference}$ are the measured SERS intensity of the TNPRs and normal Raman standard sample, respectively. [TNPR] and [reference] are the estimated number of molecules in the experiments. A saturated pMA monolayer coverage of 0.39 nm2 per molecule is used to estimate the number of molecules on a TNPR surface. 18 Assuming that an individual TNPR is a cylindrical ellipsoid particle, the maximum number of pMA molecules that can self-assemble is ~$5.1 \times 10^4$. A 0.1 mL neat liquid pMA (1.06 g/cm$^3$) droplet on a quartz substrate with a known detection volume from a 20× microscope objective was used to estimate the number of molecules for the reference sample, giving ~$4.5 \times 10^{13}$ pMA molecules. We took SERS spectra on a single TNPR at 10 different locations with exactly the same exposure time and individual Raman spectra, which are depicted in FIG. 3. Remarkably, the intensities of the measured Raman spectra are very constant, showing that fabrication repeatability of particles shapes is very reliable. Especially, the signal strengths of the 1590 and 1077 cm-1 ring modes of pMA were monitored. By looking carefully at the raw data, we found that the intensity of these two modes is very constant among measurements. The maximum SERS EF from an individual TNPR reached ~$(3.4\pm0.3)\times10^{10}$ and $(2.9\pm0.3)\times10^{10}$ at 1077 and 1590 cm-1, respectively, and the error bars were obtained from sample-to-sample variation of Raman scattering intensity. It should be noted that the possible error in estimating the surface coverage of pMA and the volume illuminated by the microscope objective obviously affects the precision in calculating the SERS EF. To provide a trustworthy estimation of the SERS EF for a TNPR, we are performing the calculation in the most conservative manner. The SERS EF was determined by assuming maximum pMA coverage over the entire TNPR metal surface and with the smallest volume being illuminated by microscope objectives. The reported value is in fact representing the lower bound of the SERS EF, and the actual EF can be even higher.

We also measured the Raman spectra on $SiO_2$-capped TNPRs to isolate the SERS contribution from the sidewall of the capped TNPRs. We assumed that there are no pMA molecules self-assembled on the SiO2 layer after copious DI water rinsing. The ratio of pMA molecules self-assembled on the exposed metal surface of the TNPR to that of the capped TNPR was assumed to be the same as the area ratio, which is about 1.6. The maximum measured SERS EF intensity on the capped TNPR reaches $(6.1\pm0.3)\times10^{10}$ and $(4.6\pm0.3)\times10^{10}$ for the 1077 and 1590 cm$^{-1}$ ring modes, respectively. The relative SERS intensity ratio for a TNPR to a capped TNPR is approximately 1.3. This is an interesting observation, since the SERS EF ratio between the capped TNPR and the TNPR is not proportional to the number of molecules assembled on the exposed metal surface.

Figure 4:
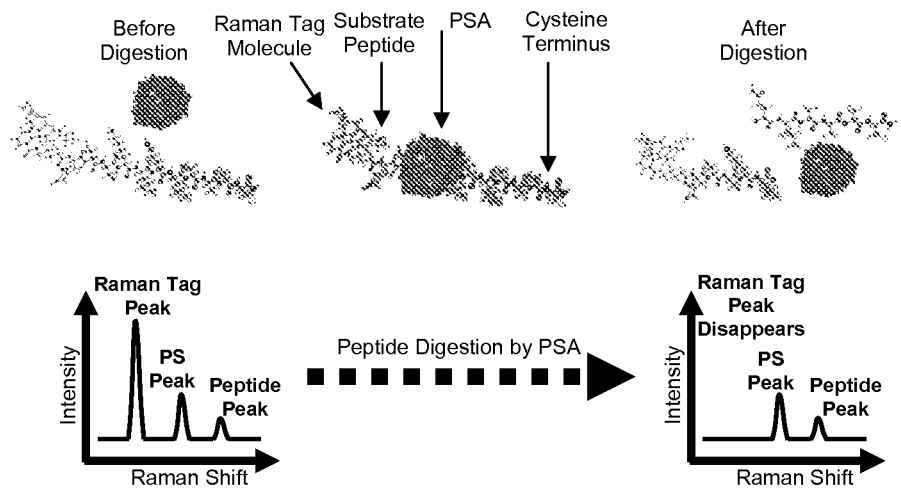
FIG. 4. PSA detection scheme using Raman detection and spectroscopy.

To understand these experimental results, we performed several numerical calculations. We applied the discrete dipole approximation (DDA) method to compute the near field distribution of the E-field surrounding the TNPR. FIG. 4 shows the calculated E-field amplitude distribution at the sidewall and top surface of a TNPR with the geometrical parameters corresponding to the SEM and AFM measurements. The permittivity of Ag is taken from the literature for bulk Ag material, and the permittivity of $SiO_2$ is set to 2.13. The substrate, which has significant effects on the plasmon resonance, is taken into account by embedding the particle in a homogeneous medium with a refractive index of 1.4, which is the averaged refractive index of air and ITO.26 FIG. 6c clearly shows an angular dipole-like E-field distribution where stronger fields are localized along the incident polarization direction θ=0 (along the TNPR long axis). The z dependence of the field shows that the strong local fields are mainly distributed close to the Ag/$SiO_2$, Ag/air, and Ag/ITO interfaces. FIG. 6b shows that the stronger fields or "hotter spots" are mainly located close to the edge of the ellipse around the direction of the incident polarization.

In summary, we studied the SERS EF of TNPRs. The observed SERS EF of a single TNPR can be as large as $6.1\times10^{10}$ when the plasmon resonance is tuned to the pump laser frequency, which is among the highest reported to date. We developed a novel technique that forces the molecules to be assembled on the sidewall of the resonator where the field is strongest, giving an accurate measurement of the Raman enhancement factor. The experimental results agree well with numerical calculations of the TNPR. Nanofabrication enables precise dimension control and accurate placement of the TNPRs, eliminating the issues resulting from aggregation and size variation effects, often associated with chemical synthesis or self-assembly of colloidal nanoparticles. Thus, it offers a unique advantage for the development of integrated biosensing devices.

EXAMPLE 2

Protease-Specific Substrate Peptide Conjugated Nprs for Real-Time Protease Detection and Measurement In this work, NPRs (FIG. 1a) were conjugated with a PSA protease-specific substrate peptide, which has the sequence R19-HSSKLQLAAAC (SEQ ID NO:1) (S. R. Denmeade, C. M. Jakobsen, S. Janssen et al., *J Natl Cancer Inst* 95 (13), 990 (2003); S. R. Denmeade, W. Lou, J. Lovgren et al., *Cancer Res* 57 (21), 4924 (1997)), with the SERS molecule Rhodamine 19 (R19) at the N-terminus and cysteine at the C-terminus (FIG. 1b). The peptide has been identified as a highly specific peptides that can be cleaved by paPSA in vivo in xenografts models (S. R. Denmeade, C. M. Jakobsen, S. Janssen et al., *J Natl Cancer Inst* 95 (13), 990 (2003)) and human samples (P. Wu, U. H. Stenman, M. Pakkala et al., *Prostate* 58 (4), 345 (2004); P. Wu, L. Zhu, U. H. Stenman et al., *Clin Chem* 50 (1), 125 (2004)). The paPSA cleaves the peptide, leading to the release of the R19 moiety (FIG. 1c) and a subsequent decrease in the Raman scattering intensity in a dose- and time-dependent manner, and the PSA protease activity can be accurately quantified. It has been theoretically estimated that SERS enhancement is strongly localized to the vicinity of nanoparticle resonator surface (5-10 nm), which effectively eliminates the assay background noise from the Raman scattering substance in the surrounding fluids, or the R19 moieties that diffuse into the solution after protease cleavage. Because of this unique property, the assay can be performed in a simplified one-step format with no additional washing step required.

Under an optical microscope, the NPR arrays were distinctly visible due to the strong scattering of light at their resonant wavelength (FIG. 1d). The magnified views of NPR arrays that measured by Scanning Electron Microscope (SEM) and Atomic Force Microscope (AFM) are showing in FIGS. 1e and 1f. The optical properties of the NPR were characterized by illuminating the NPRs with collimated light delivered by a multimode optical fiber from a 150 W Xenon lamp (Thermo Oriel) and collecting the extinction spectra using a grating spectrometer (Triax 550, Jobin Yvon) with matched liquid nitrogen cooled CCD detector (CCD-3500, Jobin Yvon) (Durant S. Su K, Steel M. J., Xiong Y. Sun C., Zhang X, *Journal of Physical Chemistry B* 110 (9), 3964 (2006)). The $SiO_2$ layer, sandwiched between the Ag layers, enable precisely tuning of NPR resonance. As shown in FIG. 1g, the measured resonance peak of NPRs-peptide-R19 conjugates closely matches laser excitation wavelength at 532 nm, and thus, maximizes the enhancement of Raman scattering. For the SERS experiments, Raman spectra were measured using a modified inverted microscope (Axiovert 200, Zeiss) with a 50× objective in a backscattering configuration. As shown in FIG. 1h, the NPR-based SERS substrate exhibits reproducible Raman spectrum with consistent enhancement factor at the same order of magnitude. The variation of experimentally measured SERS intensities obtained from 6 different SERS NPR array are below 25% and it can be normalized in the experiment.

The assay was performed by exposing the NPR-peptide nanosensor to the fluidic samples and the subsequent time-dependent R19 Raman spectra change was recorded at an interval of one minute and an integration time of 30 seconds.

Figure 2:
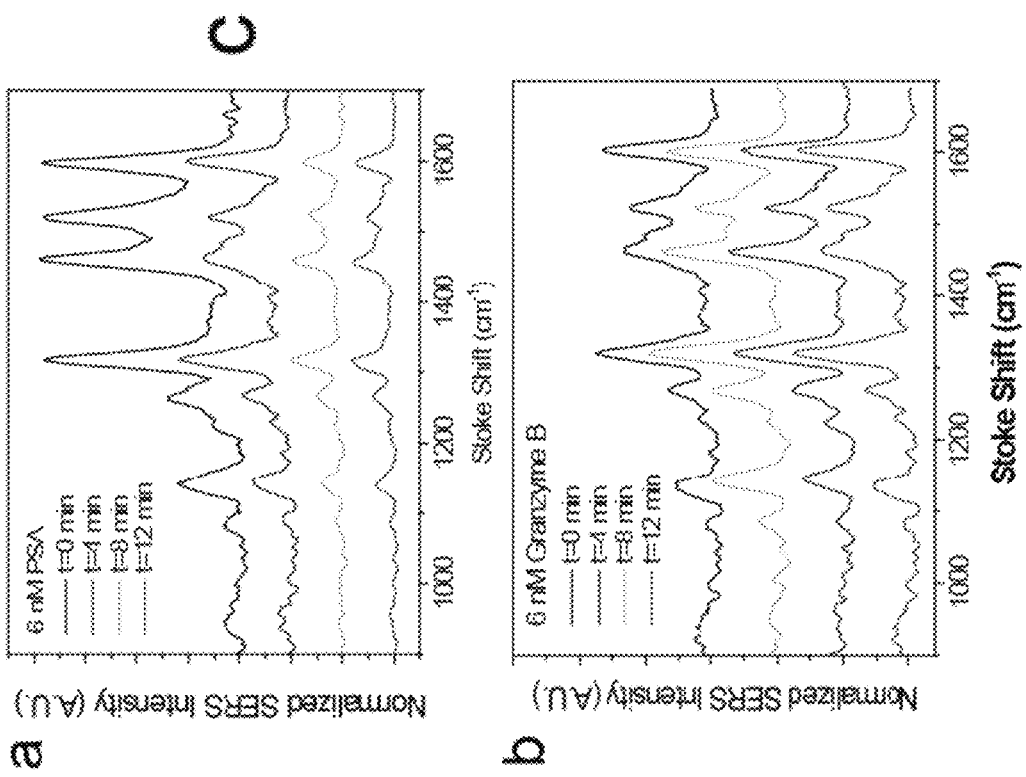
FIG. 2 Real-time kinetic measurement of PSA protease activity. (a) SERS spectra for 6 nM PSA incubation taken over 30 minutes with an integration time of 30 seconds. (b) SERS spectra for the negative control, 6 nM granzyme B, taken over 30 minutes. (c) Time-resolved measurements of relative change in Raman peak intensity at 1316 $cm^{-1}$, 1456 $cm^{-1}$, 1526 $cm^{-1}$, and 1597 $cm^{-1}$ before and after addition of PSA protease. Negative time represents time before protease addition.

The Raman 1316 cm$^{-1}$ ring breathing mode from the PSA peptide was monitored as the primary signature peak in this study, while the 1456 cm$^{-1}$, 1526 cm$^{-1}$, and 1597 cm$^{-1}$ peaks were also monitored as additional references (FIG. 2). The time-resolved spectral measurement in the presence of PSA (FIG. 2a) is plotted in FIG. 2c. Considering that the SERS intensities are proportional to the remaining R19 on the NPR surface, the normalized SERS intensity change is a direct indicator of PSA activity. Despite the variation in the initial intensity of different Raman signature peaks, the normalized data all converged into the same curve, indicating the normalized SERS intensity change is a reliable measure to quantitatively determine the substrate peptide being cleaved. As shown in FIG. 2c, before PSA addition, the NPR nanosensor showed steady intensities for all the peaks over a 10 minute period. However, upon addition of PSA, a significant decrease in each Raman peak is observed in the first 10-12 minutes, indicating that the PSA protease was able to cleave the peptides on the NPR. The decrease of the Raman signal then reaches a plateau by 30 minutes. Another serine protease, Granzyme B, was selected as a negative control (FIG. 2b-c). Within 50 minutes of recording, no substantial changes in SERS intensity was observed, even at concentrations up to 1 µM. This result demonstrates that the decrease of Raman signal in the PSA assay was based on a genuine enzymatic process, rather than a non-specific hydrolysis reaction or due to the displacement of the peptide from the surface by other components in the buffer.

The sensitivity of the NPR nanosensor was evaluated by measuring SERS intensity change of set of sample with PSA enzyme concentration ranging from 6 nM to 6 pM. The absolute value of normalized SERS intensity change is shown in FIG. 3a. As expected, the rate of decrease in the Raman signal was proportional to the concentration of PSA, which is explained by a reduced rate of peptide cleavage when the PSA concentrations decreased. The proteolytic activity eventually reaches an equilibrium stage at 30 minutes as indicated by each Raman signal reaching a plateau. The absolute value of normalized decrease in SERS intensity versus various concentrations, after 30 minutes of enzyme addition, is plotted in FIG. 3b. The dynamic range for detection, in the current assay setup, was from 6 pM to 6 nM. PSA concentration higher than 6 nM does not exhibit a distinct difference with the given detection time. As shown in FIG. 3c, the monitored Raman peak intensity exhibits distinguishable decay characteristics at different PSA concentrations during the initial 4 minutes of sampling. Thus, by fitting the decaying rate, reliable assays can possibly be accomplished in 4 minutes.

In addition to protease activity measurements of purified PSA, measurements for PSA protease activity in extracellular fluid (ECF) from live cell culture was performed (FIG. 3d). It is well known that LNCaP cells secrete PSA and have recently been used in xenografts to evaluate in vivo PSA concentration (S. R. Denmeade, C. M. Jakobsen, S. Janssen et al., *J Natl Cancer Inst* 95 (13), 990 (2003)). For comparison, a K562 cell line, which does not secrete PSA into the ECF, was used as a negative control. LNCaP ECF showed a significant change in SERS signal, while K562 exhibits very low PSA enzymatic activity (FIG. 3d). By correlating the normalized decrease in Raman signal with FIG. 3b, it was determined that the LNCaP media had an elevated amount of paPSA concentration (FIG. 3d).

Compared with fluorescence-based assay, the NPR-based method offers several advantages. Strongly localized Raman enhancement can substantially amplify the signal and also effectively reduce background noise. Therefore, it allows one-step and label free detection of protease activity with sensitivity at 6 pM, and dynamic range of 3 orders of magnitude. It should note PSA is considered a weak protease and other proteases would allow even better sensitivity. Second, it allows accurate measurement with very small sample volume. Indeed, we estimate PSA protease activity from single cells can be measured accurately (See below). Third, fabricated using well established nano-lithography process, NPR-based method is highly reproducible and thus, allowing quantitative assessment of protease activity.

Methods

NPR Fabrication

The NPR was patterned on quartz substrates (HOYA Corp.) by electron beam lithography (EBL) (Nanowriter Series EBL 100, Leica Microsystems). A 30 nm thick indium-tin-oxide (ITO) under-layer was sputtered on the substrate to prevent charging effects during the EBL process. 100 nm-thick polymathylmethacrylate (PMMA, MicroChem. Corp.) films spin-coated on the ITO-quartz glass was used as a positive photoresist. After exposure, the patterns were developed using a 1:3 ratio of MIBK and IPA mixture followed by multilayer deposition of metal and dielectric materials using electron beam evaporation (Mark 40, CHA) and standard lift-off procedures. We fabricated three layered Ag/SiO$_2$/Ag NPR arrays with each silver and SiO$_2$ layer thickness equal to 25 nm and 5 nm, respectively. The geometry of the fabricated NPR was examined by atomic force microscopy, and the total thickness of the NPR is confirmed to be 55 nm.

Device Design and Characterization

Figure 5A:
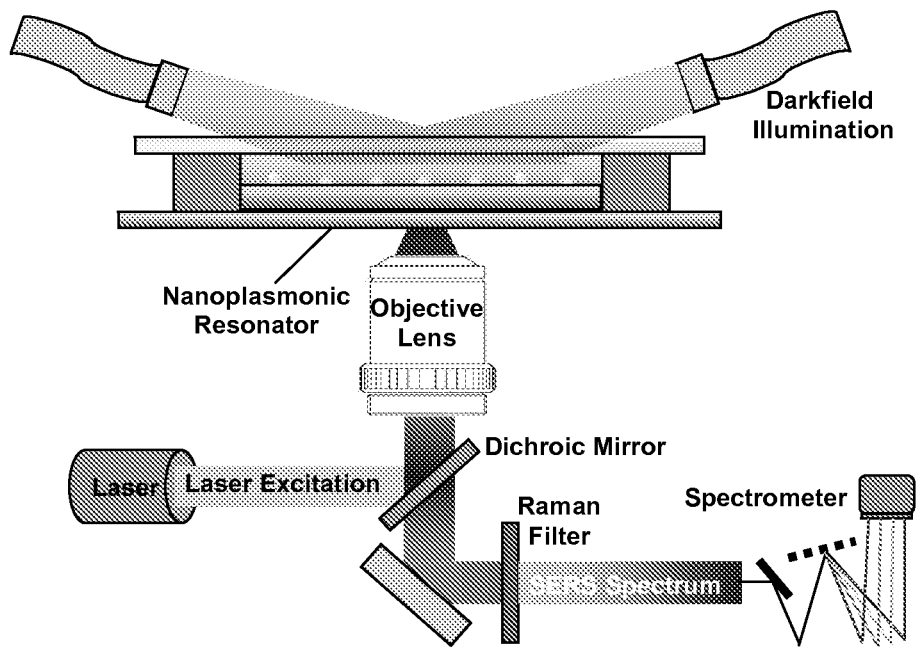
FIG. 5A. A SERS microspectroscopy system and nanoplasmonic resonator visualization and real-time enzyme reaction detection.
Figure 5B:
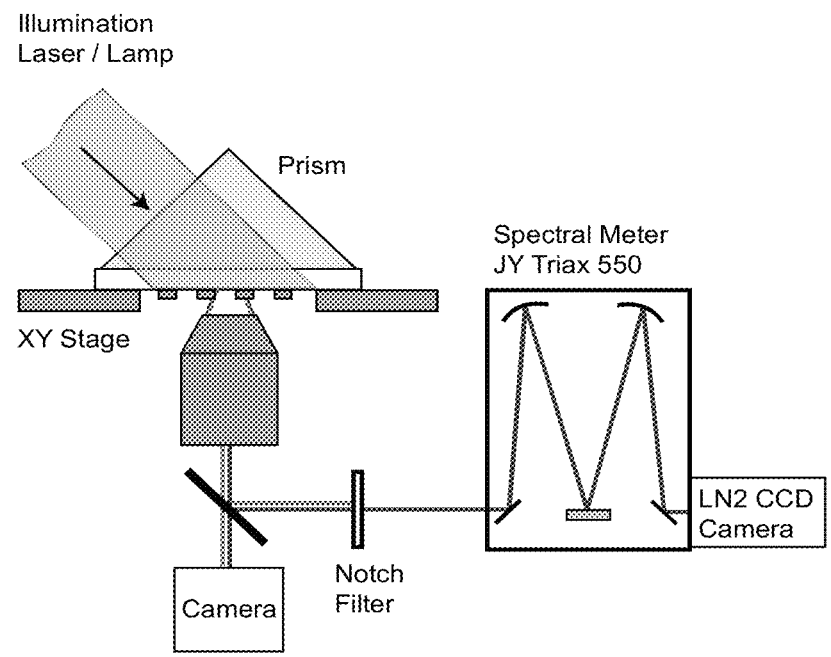
FIG. 5B. A schematic of an optical spectrum measurement setup.

Micro-region SERS measurements are performed on an inverted optical microscope (Axiovert 200, Zeiss) with matched high resolution grating spectrometer (Triax 550, Jobin Yvon). Instrumental set-up is shown in FIGS. 5A and 5B. To excite the particles plasmons, the Nanoplasmonic Resonators (NPRs) were illuminated with a collimated laser beam (Frequency doubling YAG laser, 532 nm) through a right angle prism at an angle resulting in a total internal reflection (TIR) configuration. An evanescent electromagnetic wave is generated and used to excite the particle plasmons. The samples are attached to the bottom of the prism by applying index matching oil between the sample substrate and the prism. Such sample configuration effectively eliminates all stray scattering light due to surface defects and dust particles, leading to significantly reduced background signal. The excited collective electron oscillations within the particles then radiate electromagnetic waves of the same frequency into the far field, whereby the collection and spectral measurement takes place. The scattered light from the NPRs is then collected by a 50× long working distance objective. A holographic notch filter (532 nm, Kaiser Optical System) was placed in the beam path in order to remove the illuminating beam. The emerging light is then imaged onto the entrance slit of the grating spectrometer system with a liquid Nitrogen cooled charge coupled device (CCD) camera (CCD-3500, Jobin Yvon) for spectrum analysis.

The extinction spectrum measurement was performed in a similar configuration. In this measurement, 150 W Xenon white light source has been used as the illumination source and the collimated light was delivered through an optical fiber bundle.

For the SERS experiments, Raman spectra were measured using a modified inverted microscope (Axiovert 200, Zeiss) with a 50× objective in a backscattering configuration. Baseline subtraction was applied to remove the fluorescence background of the measured spectra. The spectra were then smoothed in Matlab using the Savitsky-Golay method with a second-order polynomial and window size of 9. To correct the possible influence due to the fluctuation of illumination intensity, frequency dependence of Raman scattering, and the variation of initial packing density of the report molecules, the change in SERS intensity was normalized to the average intensity before protease addition. The normalized SERS intensity change is defined as $$\Delta I = [I_t - I_0]/I_0$$

where $I_0$ is the average SERS intensity before the addition of the protease and $I_t$ is the SERS intensity measured at the given time t.

To estimate the detection volume of the NPR array, the diffusion length is first calculated as $L_D = \sqrt{Dt} \sim 0.5$ mm where D is estimated as $1 \times 10^{-6}$ cm$^2$/s and t is 1800s. The un-normalized detection volume is then determined as $V = (L_A + L_D)^2 L_D \sim 1 \times 10^{-7}$ L where $L_A$ is the length of the NPR array (15 µm). This volume must be normalized due to the fact that the molecules have an equal likelihood to diffusion in any direction. The likelihood of these molecules coming in contact with the NPR array can be estimated based on the surface area of the array and the total surface area available for diffusion. This probability of molecules can diffuse to the NPR array is then given by:

$$W_{Det} = \frac{L_A^2}{6L_D^2} \sim 1.5 \times 10^{-4}$$

assuming the NPR array surface area of the array is much smaller than the available diffusion surface area. The total sampling volume is then calculated as $V_{Det} = W_{Det} V \sim 15$ pL.

Peptide Synthesis

R6G-Ava-HSSKLQLAAAC-NH$_2$ (SEQ ID NO:1). (2). 401 mg (0.277 mmol) of Rink Amide AM polystyrene resin (loading 0.69 mmol/g) was added to a 12 mL fitted syringe and swollen with NMP (4 mL). The Fmoc protecting group was removed by treatment with 1:2:2 piperidine/NMP/CH$_2$Cl$_2$ solution (3 mL) for 30 min, and the resin was filtered and washed with NMP (3×3 mL) and CH$_2$Cl$_2$ (3×3 mL). To load the α-amino acid residues, the resin was subjected to repeated cycles of coupling conditions (method A or method B), followed by washing (5×3 mL NMP, 5×3 mL CH$_2$Cl$_2$), Fmoc deprotection [treatment with 1:2:2 piperidine/NMP/CH$_2$Cl$_2$ solution (3 mL) for 30 min], and washing again with NMP (5×3 mL) and CH$_2$Cl$_2$ (5×3 mL). The first α-amino acid residue was loaded by addition of a preformed solution of Fmoc-Cys(Trt)-OH (1.17 g, 2.00 mmol), PyBOP (1.04 g, 2.00 mmol), and HOBt (270 mg, 2.00 mmol) in 1:1 NMP/CH$_2$Cl$_2$ (2 mL) onto the resin and the resulting slurry was stirred for 5 min on a wrist-action shaker, followed by addition of i-Pr$_2$EtN (0.55 mL, 4.0 mmol). The reaction was allowed to proceed for 5 h. The resin was then filtered, washed (5×3 mL NMP, 5×3 mL CH$_2$Cl$_2$), and dried under high vacuum. The loading of Cys was determined to be 0.60 mmol/g (78% yield). Successive couplings were achieved either by method A or method B. Method A consists of addition a preformed solution of Fmoc-protected amino acid [Fmoc-Cys(Trt)-OH (1.17 g, 2.00 mmol), Fmoc-Ala-OH (622 mg, 2.00 mmol), Fmoc-Leu-OH (707 mg, 2.00 mmol), Fmoc-Gln(Trt)-OH (1.22 g, 2.00 mmol), Fmoc-Ser(tBu)-OH (767 mg, 2.00 mmol), and Fmoc-His(Trt)-OH (1.24 g, 2.00 mmol)], PyBOP (1.04 g, 2.00 mmol), and HOBt (270 mg, 2.00 mmol) in NMP/CH$_2$Cl$_2$ (1:1, 2 mL), followed by addition of i-Pr$_2$EtN (0.55 mL, 4.0 mmol). The reactions were allowed to proceed for at least 4 h. Method B consists of subjection of the resin to a 0.4 M solution of the suitably protected acid [Fmoc-Lys(Boc)-OH (375 mg)], which had been pre-activated by incubation with DIC (130 µL, 0.84 mmol) and HOBt (108 mg, 0.800 mmol) in DMF (2 mL) for 10 min. The coupling was allowed to proceed for 4 h. After each coupling the resin was filtered and washed (NMP: 5×3 mL, CH$_2$Cl$_2$: 5×3 mL), followed by removal of the Fmoc protecting group. After coupling and deprotection of the final α-amino acid residue, the Ava linker was added by subjection of the resin to a 0.4 M solution of Fmoc-S-Ava-OH (272 mg, 0.800 mmol) which had been pre-activated by incubation with DIC (120 µL, 0.80 mmol) and HOBt (108 mg, 0.800 mmol) in N-methylpyrrolydinone (1 mL) for 10 min. The coupling was allowed to proceed overnight. The resin was filtered and washed (5×3 mL NMP, 5×3 mL CH$_2$Cl$_2$), the Fmoc protecting group was removed, and the resin washed again. The rhodamine group was incorporated by adding a 0.4 M solution of rhodamine 19 (412 mg, 0.8 mmol), which had been pre-activated by incubation with DIC (130 µL, 0.84 mmol) and HOBt (108 mg, 0.800 mmol) in NMP (2 mL) for 10 min. The reaction was allowed to proceed for 6 h, the coupling procedure was repeated once more and the reaction was allowed to proceed overnight. The substrate was cleaved from the resin by incubation with a solution of 94:2:2:2 TFA/triisopropylsilane/H$_2$O/ethanedithiol (3 mL) for 2 h, purified using preparatory C18 reverse-phase HPLC (CH$_3$CN/H$_2$O-0.1% TFA, 5-95% for 50 min, 20 mL/min, 220/254/280 nm detection for 100 min, $t_R$=24.3 min), and lyophilized. MS (MALDI), m/z calcd for C$_{78}$H$_{116}$N$_{19}$O$_{17}$S: 1622.85. Found: m/z 1623.90.

Peptide Conjugation to NPR

The peptide attaches to the NPR via the thiol group on cysteine. The PSA substrate peptides mixed with octanethiol at a 1:3 ratio were incubated for 24 hours to ensure a well-ordered self-assembled monolayer (SAM) on the NPR metallic surface. Octanethiol, with a SAM chain length of 1-2 nm, was used as packing material to manage the distance among the PSA substrate peptides and help to erect the PSA substrate peptide for optimal spatial presentation. Thus, the octanethiol SAM improves access for the protease to bind to the peptides.

Cell Culture and Clinical Semen Samples

LNCaP cells actively secrete PSA into ECF, and the human CML cells K562 are negative for PSA. Both cell lines are maintained in RPMI-1640 with 10% FBS and 1× Pen/Strep, at 37° C. with 5% CO$_2$. 10×10$^6$ cells were cultured overnight in 10 ml fresh media. Media from both cultures were collected and PSA activity was measured by fluorescent methods as described before, and calibrated against commercial PSA (Calbiochem, San Diego, Calif.). Briefly, the PSA-binding peptides and derivatives with a spacer were chemically synthesized and used to prepare an affinity column, which was used to fractionate PSA in seminal plasma.

Purified PSA Preparation and Proteolytic Reaction

Proteolytically active PSA was purified to homogeneity from human seminal plasma by column chromatography, eliminating all known PSA complexes and retaining its protease fraction. Cleavage of the substrate peptide immobilized on the NPR nanosensor is performed in a buffer of 50 mM Tris-HCl, pH 8.0, 100 mM NaCl, and 0.1 mM EDTA, and the reaction was monitored in real-time in 37° C. Protease inhibitors (to prevent PSA and Granzyme B degradation) are obtained from CalBiochem and added to the reaction following the manufacturer's instructions, so that the final reaction solution contains 5 µM AEBSF, 4.2 nM Aprotinin, 200 nM Elastatinal and 10 nM GGACK. The concentration of proteolytically active PSA in the PSA reagent has been prepared with a wide range of concentration from 6 pM to 6 nM.

The present examples, methods, procedures, specific compounds and molecules are meant to exemplify and illustrate the invention and should in no way be seen as limiting the scope of the invention. Any patents, publications, publicly available sequences mentioned in this specification and below are indicative of levels of those skilled in the art to which the invention pertains and are hereby incorporated by reference to the same extent as if each was specifically and individually incorporated by reference.

What is claimed is:

1. A nanoplasmonic resonator (NPR) comprising nanodisks with alternating dielectric shielding layer(s), having a peptide linked to a Ramen active tag, said peptide comprising a sequence that can be specifically modified or cleaved by an enzyme and where said peptide is conjugated or tethered to the surface of the nanoplasmonic resonator, wherein said resonator provides sufficient sensitivity to detect modification or cleavage of said peptide by said enzyme, and wherein said nanodisks comprise a noble metal or transitional metal/metal oxides capable of creating nanoplasmonic resonance.

2. The resonator of claim 1 wherein the tag is a Raman active tag for surface enhanced Raman scattering (SERS) detection.

3. The resonator of claim 1 wherein the tag is a fluorescent or other Raman detectable moiety.

4. The resonator of claim 1, wherein the shielding layer comprises a material selected from the group consisting of silicon dioxide, quartz, polystyrene, silica, and dextran.

5. The resonator of claim 4, wherein the nanodisk comprises silver.

6. The resonator of claim 4, wherein the nanodisk comprises gold.

7. The resonator of claim 1, wherein said peptide is the peptide R6G-A va-HSSKLQLAAAC-NH2 (SEQ ID NO:1).

8. The resonator of claim 1, wherein the nanodisk comprises a metal selected from the group consisting of gold, silver, platinum, and copper.

9. The resonator of claim 1, wherein the nanodisk comprises platinum or copper.

10. The resonator of claim 8, wherein the shielding layer-comprises a material selected from the group consisting of silicon dioxide, quartz, polystyrene, silica, and dextran.

11. The resonator of claim 1, wherein the nanodisk comprises silver.

12. The resonator of claim 1, wherein the nanodisk comprises gold.

13. The resonator of claim 1, wherein said resonator comprises alternating layers of silver and $SiO_2$.

14. A method useful for in vitro detection and measurement of enzymatic activity in a sample, said method comprising:
  providing a peptide conjugated nanoplasmonic resonator according to any one of claims 1-13;
  contacting said nanoplasmonic resonator with said sample; and
  detecting protease cleavage or modification of said peptide by SERS detection, where said nanoplasmonic resonator provides single-step detection of enzymatic activity.

15. The method of claim 14, wherein said nanoplasmonic resonator provides detection at least nanomolar sensitivity.

16. The method of claim 14, wherein said nanoplasmonic resonator provides detection at picomolar sensitivity.

17. The method of claim 14, wherein the nanodisks are 50 nm to 500 nm in diameter.

* * * * *